(12) United States Patent
Boral et al.

(10) Patent No.: US 9,233,968 B1
(45) Date of Patent: Jan. 12, 2016

(54) KINASE INHIBITORS

(71) Applicant: Allergan, Inc., Irvine, CA (US)

(72) Inventors: Sougato Boral, Irvine, CA (US);
Shimiao Wang, Tustin, CA (US);
Thomas C. Malone, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/524,256

(22) Filed: Oct. 27, 2014

(51) Int. Cl.
*A61K 31/5025* (2006.01)
*A61K 31/416* (2006.01)
*C07D 487/04* (2006.01)
*C07D 231/56* (2006.01)

(52) U.S. Cl.
CPC ............ *C07D 487/04* (2013.01); *A61K 31/416* (2013.01); *A61K 31/5025* (2013.01); *C07D 231/56* (2013.01)

(58) Field of Classification Search
None
See application file for complete search history.

(56) References Cited

U.S. PATENT DOCUMENTS 5,137,901 A    8/1992  Junge et al.

FOREIGN PATENT DOCUMENTS

WO    2014/040549    *  3/2014

OTHER PUBLICATIONS

Adamis, A., et al., Inhibition of Platelet-Derived Growth Factor B Signaling Enhances the Efficacy of Anti-Vascular Endothelial Growth Factor Therapy in Multiple Models of Ocular Neovascularization, Amer. Journal Pathology 2006, 168: 2036-2053, 6.
Aora, A., et al., Role of Tyrosine Kinase Inhibitors in Cancer Therapy, J. Pharma. & Exp. Therapeutics 2015, 315: 971-979, 3.
Baraket, M., et al., VEGF inhibitors for the treatment of neovascular age-related macular degeneration, Informa Healthcare, 2009, 637-646.
Bergers, G., et al., Benefits of targeting both pericytes and endothelial cells in the tumor vasculature with kinase inhibitors, J. Clin. Invest. 2003, 111: 1287-1295, 9.
Chappelow, A., et al., Neovascular Age-Related Macular Degeneration Potential Therapies, Drugs 2008, 68: 1029-1036, 8.
Cowan-Jacob, S.W., Structural biology of protein tyrosine kinases, Cell. Mol. Life Sci. 2006, 63: 2608-2625.
Cross, L.C., et al., Rules for the Nomenclature of Organic Chemistry, Section E: Stereochemistry, Pure & Appl. Chem. 1976, 45: 11-30.
DePinho, R. et al., Coactivation of Receptor Tyrosine Kinases Affects the Response of Tumor Cells to Targeted Therapies, Science 2007, 318: 287-291.
Stahl, P.H., et al., Handbook of Pharmaceutical Salts, Properties, Selection, and Use, 2002, 329-345.
Heidenreich, R., et al., Angiogenesis: The New Potential Target for the Therapy of Psoriasis?, Drug News Perspect 2008, 21:97-105, 2.
Ni, Z., et al., Emerging Pharmacologic Therapies for Wet Age-Related Macular Degeneration, Ophthalmologica 2009, 223: 401-410.
Smith, J., et al., Expression of vascular endothelial growth factor and its receptors in rosacea, Br. J. Ophthalmol. 2007, 91: 226-229.
Zhang, X., et al., Vascular endothelial growth factor-A: A multifunctional molecular player in diabetic retinopathy, Int'l. J. Biochem. & Cell Biol. 2009, 41: 2368-2371.
Castro, J., et al., Enhancement of Oral Absorption in Selective 5-HT1D Receptor Agonists: Fluorinated 3-[3-(Piperidin-1-yl)propyl]indoles, J. Med. Chem. 1998, 41: 2667-2670.
Glennon, R.A., Concepts for the design of 5-HT1A serotonin agonists and antagonists, Drug Development Research 1992, 26: 251-274 (3).

* cited by examiner

*Primary Examiner* — Emily Bernhardt
(74) *Attorney, Agent, or Firm* — Jonathan Bass

(57) ABSTRACT

Described herein are compounds which in some embodiments are capable of modulating, regulating, and/or inhibiting tyrosine kinase signal transduction, as well as methods and compositions related to the compounds.

6 Claims, No Drawings

KINASE INHIBITORS

FIELD

The present invention relates to compounds which in some embodiments are capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cancer, blood vessel proliferative disorders, fibrotic disorders, neurodegenerative diseases, treatment of mesangial cell proliferative disorders and metabolic diseases, diabetic retinopathy, age-related macular degeneration, retinopathy of prematurity, arthritis, restenosis, hepatic cirrhosis, atherosclerosis, psoriasis, diabetes mellitus, wound healing, inflammation and neurodegenerative diseases.

BACKGROUND

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They can be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The receptor-type tyrosine kinases (RTKs) comprise a large family of transmembrane receptors with diverse biological activities. The intrinsic function of RTKs is activated upon ligand binding, which results in phosphorylation of the receptor and multiple cellular substrates, and subsequently in a variety of cellular responses. The non-receptor tyrosine kinases represent a collection of cellular enzymes which lack extracellular and transmembrane sequences. A more detailed discussion of receptor and non-receptor tyrosine kinases is provided in Cowan-Jacob Cell Mol. Life Sci., 2996, 63, 2608-2625

There are a number of examples where RTK kinases, have been found to be involved in cellular signaling pathways leading to pathological conditions, including exudative age-related macular degeneration (Ni et al. *Opthalmologica* 2009 223 401-410; Chappelow et al. *Drugs* 2008 68 1029-1036), diabetic retinopathy (Zhang et al., *Int. J. Biochem. Cell Biol.* 2009 41 2368-2371), cancer (Aora et al. *J. Path. Exp. Ther.* 2006, 315, 971), psoriasis (Heidenreich et al *Drug News Perspective* 2008 21 97-105), rosacea (Smith, J. R., V. B. Lanier, et al. *Br J Ophthalmol* 2007, 91(2): 226-229) and hyper immune response. In ophthalmic diseases such as exudative age-related macular degeneration and diabetic retinopathy aberrant activation of VEGF receptors can lead to abnormal blood vessel growth. The importance of VEGFR signaling in the exudative age-related macular degeneration disease process is evident by the clinical success of multiple anti-VEGF targeting agents including LUCENTIS®, AVASTIN®, and EYLEATM® (Barakat et al., *Expert Opin. Investig. Drugs* 2009, 18, 637). Recently it has been suggested that inhibition of multiple RTK signaling pathways may provide a greater therapeutic effect than targeting a single RTK signaling pathway. For example in neovascular ocular disorders such as exudative age-related macular degeneration and diabetic retinopathy the inhibition of both VEGFR and PDGFRβ may provide a greater therapeutic effect by causing regression of existing neovascular blood vessels present in the disease (Adamis et al., *Am. J. Pathol.* 2006 168 2036-2053). In cancer inhibition of multiple RTK signaling pathways has been suggested to have a greater effect than inhibiting a single RTK pathway (DePinho et al., *Science* 2007 318 287-290; Bergers et al. *J. Clin Invest.* 2003 111 1287-1295).

The identification of effective small compounds which specifically inhibit signal transduction by modulating the activity of receptor and non-receptor tyrosine kinases to regulate and modulate abnormal or inappropriate cell proliferation is therefore desirable and one object of this invention.

SUMMARY

The present invention relates to compounds which in some embodiments are capable of modulating, regulating and/or inhibiting tyrosine kinase signal transduction by blocking the VEGF and/or PDGF receptors. Such compounds are useful for the treatment of diseases related to unregulated tyrosine kinase signal transduction, including cancer, blood vessel proliferative disorders, fibrotic disorders, and neurodegenerative diseases. In particular compounds of the present invention are useful for the treatment of mesangial cell proliferative disorders and metabolic diseases, diabetic retinopathy, age-related macular degeneration, retinopathy of prematurity, arthritis, restenosis, hepatic cirrhosis, atherosclerosis, psoriasis, diabetes mellitus, wound healing, inflammation and neurodegenerative diseases.

In particular, in one aspect, the present invention relates to compounds represented by Formula I:

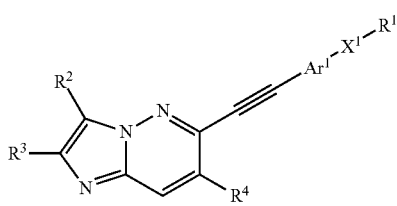

I or a pharmaceutically acceptable salt thereof, wherein:
Ar$^1$ is selected from the group consisting of substituted or unsubstituted aryl and substituted or unsubstituted heteroaryl;
X$^1$ is selected from the group consisting of:

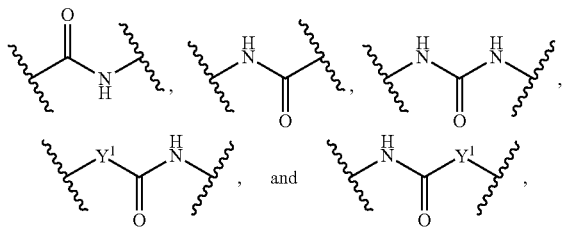

wherein Y$^1$ is selected from the group consisting of O, CR$^a$R$^b$, and NR$^c$, and wherein R$^a$ and R$^b$ are independently selected from the group consisting of hydrogen and C$_1$ to C$_8$ alkyl, and R$^c$ is C$_1$ to C$_8$ alkyl;
R$^1$ is selected from the group consisting of substituted or unsubstituted aryl and substituted or unsubstituted heteroaryl;
R$^2$ is selected from the group consisting of hydrogen and halogen;
R$^3$ is selected from the group consisting of hydrogen, C$_1$ to C$_8$ alkyl, $(CR^5R^6)_aC(O)OR^7$, $(CR^5R^6)_aOR^7$, $(CR^5R^6)_aN(R^{10})C(O)R^7$, $(CR^5R^6)_aC(O)N(R^8)R^9$, $(CR^5R^6)_aN(R^{10})C(O)OR^7$, $(CR^5R^6)_aN(R^{10})C(O)N(R^8)R^9$, and $(CR^5R^6)_aN(R^8)R^9$;
R$^4$ is selected from the group consisting of hydrogen, halogen, and C$_1$ to C$_8$, alkyl;
R$^5$ is selected from the group consisting of hydrogen, C$_1$ to C$_8$ alkyl, fluoro, hydroxy, hydroxymethyl, C(O)CH$_3$, CH$_2$CH$_2$OH, CH$_2$CH$_2$CH$_2$OH and CH$_2$CH$_2$OCH$_2$CH$_2$OH;
R$^6$ is selected from the group consisting of hydrogen, C$_1$ to C$_8$ alkyl, hydroxy, and fluoro;
R$^7$ is selected from the group consisting of hydrogen, C$_1$ to C$_8$ alkyl, substituted or unsubstituted aryl, substituted or unsubstituted heteroaryl, halogen, hydroxy, hydroxymethyl, COCH$_3$, CH$_2$CH$_2$OH and CH$_2$CH$_2$CH$_2$OH;
R$^8$ is selected from the group consisting of hydrogen, C$_1$ to C$_8$ alkyl, substituted or unsubstituted aryl, substituted or unsubstituted heteroaryl, halogen, hydroxy, hydroxymethyl, COCH$_3$, CH$_2$CH$_2$OH and CH$_2$CH$_2$CH$_2$OH; or R$^8$ together with R$^9$ forms a substituted or unsubstituted heterocyclic ring;
R$^9$ is selected from the group consisting of hydrogen, C$_1$ to C$_8$ alkyl, substituted or unsubstituted aryl, substituted or unsubstituted heteroaryl, halogen, hydroxy, hydroxymethyl, COCH$_3$, CH$_2$CH$_2$OH and CH$_2$CH$_2$CH$_2$OH; or R$^9$ together with R$^8$ forms a substituted or unsubstituted heterocyclic ring;
R$^{10}$ is selected from the group consisting of hydrogen, C$_1$ to C$_8$ alkyl, fluoro, hydroxy, hydroxymethyl, C(O)CH$_3$, CH$_2$CH$_2$OH, CH$_2$CH$_2$CH$_2$OH and CH$_2$CH$_2$OCH$_2$CH$_2$OH; and
a is 0, 1, 2, 3, 4, or 5.

In another aspect, the invention relates to a compound represented by Formula VII:

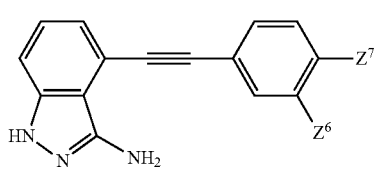

VII or a pharmaceutically acceptable salt thereof, wherein one of Z$^6$ and Z$^7$ is independently hydrogen and the other is independently:

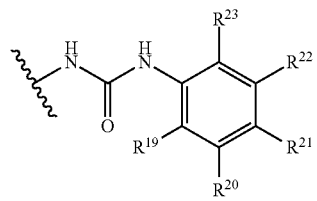

wherein R$^{19}$ to R$^{23}$ are independently selected from the group consisting of hydrogen, methyl, trifluoromethyl, OR$^{24}$, N(R$^{25}$)R$^{26}$, and halogen; R$^{24}$ to R$^{26}$ are independently C$_1$ to C$_8$ alkyl.

In another aspect, the invention relates to a pharmaceutical composition comprising as active ingredient a therapeutically effective amount of one or more of the compounds described herein and a pharmaceutically acceptable adjuvant, diluent or carrier.

DETAILED DESCRIPTION

The present invention relates to compounds capable of modulating, regulating and/or, inhibiting tyrosine kinase signal transduction by blocking the VEGF and/or PDGF receptors, as well as related methods and compositions.

The term "alkyl", as used herein, refers to saturated, monovalent or divalent hydrocarbon moieties having linear or branched moieties or combinations thereof and containing 1 to 12 carbon atoms. One methylene (—CH$_2$—) group of the alkyl group can be replaced by oxygen, sulfur, sulfoxide, nitrogen, carbonyl, carboxyl, sulfonyl, sulfate, sulfonate, amide, sulfonamide, by a divalent C$_{3-8}$ cycloalkyl, by a divalent heterocycle, or by a divalent aryl group. Alkyl groups can have one or more chiral centers. Alkyl groups can be independently substituted by halogen atoms, hydroxyl groups, cycloalkyl groups, amino groups, heterocyclic groups, aryl groups, carboxylic acid groups, phosphonic acid groups, sulphonic acid groups, phosphoric acid groups, nitro groups, amide groups, sulfonamide groups, ester groups, ketone groups.

The term "cycloalkyl", as used herein, refers to a monovalent or divalent group of 3 to 8 carbon atoms derived from a saturated cyclic hydrocarbon. Cycloalkyl groups can be monocyclic or polycyclic. Cycloalkyl can be independently substituted by halogen atoms, sulfonyl $C_{1-8}$ alkyl groups, sulfoxide $C_{1-8}$ alkyl groups, sulfonamide groups, nitro groups, cyano groups, —$OC_{1-8}$ alkyl groups, —$SC_{1-8}$ alkyl groups, —$C_{1-8}$ alkyl groups, —$C_{2-6}$ alkenyl groups, —$C_{2-6}$ alkynyl groups, ketone groups, alkylamino groups, amide groups, amino groups, aryl groups, $C_{3-8}$ cycloalkyl groups or hydroxyl groups.

The term "cycloalkenyl", as used herein, refers to a monovalent or divalent group of 3 to 8 carbon atoms derived from a saturated cycloalkyl having at least one double bond. Cycloalkenyl groups can be monocyclic or polycyclic. Cycloalkenyl groups can be independently substituted by halogen atoms, sulfonyl groups, sulfoxide groups, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, ketone groups, alkylamino groups, amide groups, amino groups, aryl groups, $C_{3-8}$ cycloalkyl groups or hydroxyl groups.

The term "halogen", as used herein, refers to an atom of chlorine, bromine, fluorine, or iodine.

The term "alkenyl", as used herein, refers to a monovalent or divalent hydrocarbon radical having 2 to 6 carbon atoms, derived from a saturated alkyl, having at least one double bond. One methylene (—$CH_2$—) group, of the alkenyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. $C_{2-6}$ alkenyl can be in the E or Z configuration. Alkenyl groups can be substituted by alkyl groups, as defined above or by halogen atoms.

The term "alkynyl", as used herein, refers to a monovalent or divalent hydrocarbon radical having 2 to 6 carbon atoms, derived from a saturated alkyl, having at least one triple bond. One methylene (—$CH_2$—) group, of the alkynyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkynyl groups can be substituted by alkyl groups, as defined above, or by halogen atoms.

The term "heterocycle" as used herein, refers to a 3 to 10 membered ring, which can be aromatic or non-aromatic, saturated or unsaturated, containing at least one heteroatom selected form oxygen, nitrogen, sulfur, or combinations of at least two thereof, interrupting the carbocyclic ring structure. The heterocyclic ring can be interrupted by a C═O; the S and N heteroatoms can be oxidized. Heterocycles can be monocyclic or polycyclic. Heterocyclic ring moieties can be substituted by halogen atoms, sulfonyl groups, sulfoxide groups, nitro groups, cyano groups, —$OC_{1-6}$ alkyl groups, —$SC_{1-6}$ alkyl groups, —$C_{1-8}$ alkyl groups, —$C_{2-6}$ alkenyl groups, —$C_{2-6}$ alkynyl groups, amide groups, ketone groups, alkylamino groups, amino groups, aryl groups, ester groups, ketone groups, carboxylic acid groups, $C_{3-8}$ cycloalkyl groups or hydroxyl groups.

The term "aryl" as used herein, refers to an organic moiety derived from an aromatic hydrocarbon consisting of a ring containing 6 to 10 carbon atoms, by removal of one hydrogen atom. Aryl can be substituted by halogen atoms, sulfonyl $C_{1-6}$ alkyl groups, sulfoxide $C_{1-6}$ alkyl groups, sulfonamide groups, carboxcyclic acid groups, $C_{1-6}$ alkyl carboxylates (ester) groups, amide groups, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, ketone groups, aldehydes, alkylamino groups, amino groups, aryl groups, $C_{3-8}$ cycloalkyl groups or hydroxyl groups. Aryls can be monocyclic or polycyclic.

The term "heteroaryl" as used herein refers to an aryl moiety in which one or more of the carbons that make up the aromatic hydrocarbon ring is replaced with a heteroatom selected form oxygen, nitrogen, or sulfur. Heteroaryl can be substituted by halogen atoms, sulfonyl $C_{1-6}$ alkyl groups, sulfoxide $C_{1-6}$ alkyl groups, sulfonamide groups, carboxcyclic acid groups, $C_{1-6}$ alkyl carboxylates (ester) groups, amide groups, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, ketone groups, aldehydes, alkylamino groups, amino groups, aryl groups, $C_{3-8}$ cycloalkyl groups or hydroxyl groups. Heteroaryl can be monocyclic or polycyclic.

The term "hydroxyl" as used herein, represents a group of formula "—OH".

The term "carbonyl" as used herein, represents a group of formula "—C(O)—".

The term "ketone" as used herein, represents an organic compound having a carbonyl group linked to a carbon atom such as —C(O)$R^x$ wherein $R^x$ can be alkyl, aryl, cycloalkyl, cycloalkenyl, heterocycle as defined above.

The term "ester" as used herein, represents an organic compound having a carbonyl group linked to a carbon atom such as —C(O)O$R^x$ wherein $R^x$ can be alkyl, aryl, cycloalkyl, cycloalkenyl, heterocycle as defined above.

The term "amine" as used herein, represents a group of formula "—$NR^xR^y$", wherein $R^x$ and $R^y$ can be the same or independently H, alkyl, aryl, cycloalkyl, cycloalkenyl, heterocycle as defined above.

The term "carboxyl" as used herein, represents a group of formula "—C(O)O—".

The term "sulfonyl" as used herein, represents a group of formula "—$SO_2$—".

The term "sulfate" as used herein, represents a group of formula "—O—S(O)$_2$—O—".

The term "sulfonate" as used herein, represents a group of the formula "—S(O)$_2$—O—".

The term "carboxylic acid" as used herein, represents a group of formula "—C(O)OH".

The term "nitro" as used herein, represents a group of formula "—$NO_2$".

The term "cyano" as used herein, represents a group of formula "—CN".

The term "amide" as used herein, represents a group of formula "—C(O)$NR^xR^y$," or "$NR^xR^yC(O)$—" wherein $R^x$ and $R^y$ can be the same or independently H, alkyl, aryl, cycloalkyl, cycloalkenyl, heterocycle as defined above.

The term "sulfonamide" as used herein, represents a group of formula "—S(O)$_2NR^xR^y$" wherein $R^x$ and $R^y$ can be the same or independently H, alkyl, aryl, cycloalkyl, cycloalkenyl, heterocycle as defined above.

The term "sulfoxide" as used herein, represents a group of formula "—S(O)—".

The term "phosphonic acid" as used herein, represents a group of formula "—P(O)(OH)$_2$".

The term "phosphoric acid" as used herein, represents a group of formula "—OP(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Other defined terms are used throughout this specification:

"Ac" refers to acetyl
"aq" refers to aqueous
"eq" refers to equivalent
"DCM" refers to dichloromethane
"DMF" refers to N,N-dimethylformamide
"Et" refers to ethyl
"EtOAc" refers to ethyl acetate
"Hex" refers to hexane
"iPr" refers to i-propyl
"iPrOH" refers to isopropanol
"Me" refers to methyl
"MeOH" refers to methanol
"PDGF" refers to platelet derived growth factor
"Ph" refers to phenyl
"PTKs" refers to protein tyrosine kinase
"RTKs" refers to receptor tyrosine kinase
"rt" refers to room temperature
"tBu" refers to t-butyl.
"THF" refers to tetrahydrofuran
"VEGF" refers to vascular endothelial growth factor
"VEGFR" refers to vascular endothelial growth factor receptor In some embodiments, compounds of the present invention are represented by Formula I:

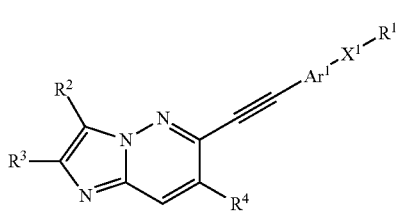

I or a pharmaceutically acceptable salt thereof, wherein:
$Ar^1$ is selected from the group consisting of substituted or unsubstituted aryl and substituted or unsubstituted heteroaryl;
$X^1$ is selected from the group consisting of:

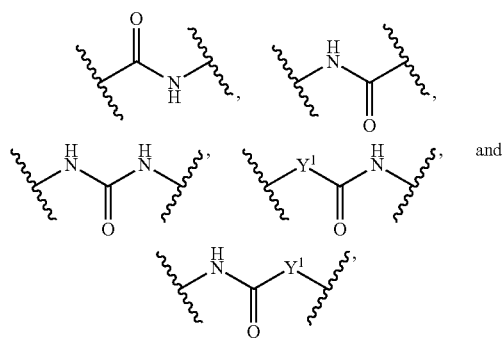

and wherein $Y^1$ is selected from the group consisting of O, $CR^aR^b$, and $NR^c$, and wherein $R^a$ and $R^b$ are independently selected from the group consisting of hydrogen and $C_1$ to $C_8$ alkyl, and $R^c$ is $C_1$ to $C_8$ alkyl;
$R^1$ is selected from the group consisting of substituted aryl and heteroaryl;

$R^2$ is selected from the group consisting of hydrogen and halogen;
$R^3$ is selected from the group consisting of hydrogen, $C_1$ to $C_8$ alkyl, $(CR^5R^6)_aC(O)OR^7$, $(CR^5R^6)_aOR^7$, $(CR^5R^6)_aN(R^{10})C(O)R^7$, $(CR^5R^6)_aC(O)N(R^8)R^9$, $(CR^5R^6)_aN(R^{10})C(O)OR^7$, $(CR^5R^6)_aN(R^{10})C(O)N(R^8)R^9$, and $(CR^5R^6)_aN(R^8)R^9$;
$R^4$ is selected from the group consisting of hydrogen, halogen, and $C_1$ to $C_8$, alkyl,
$R^5$ is selected from the group consisting of hydrogen, $C_1$ to $C_8$ alkyl, fluoro, hydroxy, hydroxymethyl, $C(O)CH_3$, $CH_2CH_2OH$, $CH_2CH_2CH_2OH$ and $CH_2CH_2OCH_2CH_2OH$;
$R^6$ is selected from the group consisting of hydrogen, $C_1$ to $C_8$ alkyl, hydroxy, and fluoro;
$R^7$ is selected from the group consisting of hydrogen, $C_1$ to $C_8$ alkyl, substituted or unsubstituted aryl, substituted or unsubstituted heteroaryl, halogen, hydroxy, hydroxymethyl, $COCH_3$, $CH_2CH_2OH$ and $CH_2CH_2CH_2OH$;
$R^8$ is selected from the group consisting of hydrogen, $C_1$ to $C_8$ alkyl, substituted or unsubstituted aryl, substituted or unsubstituted heteroaryl, halogen, hydroxy, hydroxymethyl, $COCH_3$, $CH_2CH_2OH$ and $CH_2CH_2CH_2OH$; or $R^8$ together with $R^9$ forms a substituted or unsubstituted heterocyclic ring;
$R^9$ is selected from the group consisting of hydrogen, $C_1$ to $C_8$ alkyl, substituted or unsubstituted aryl, substituted or unsubstituted heteroaryl, halogen, hydroxy, hydroxymethyl, $COCH_3$, $CH_2CH_2OH$ and $CH_2CH_2CH_2OH$; or $R^9$ together with $R^8$ forms a substituted or unsubstituted heterocyclic ring;
$R^{10}$ is selected from the group consisting of hydrogen, $C_1$ to $C_8$ alkyl, fluoro, hydroxy, hydroxymethyl, $C(O)CH_3$, $CH_2CH_2OH$, $CH_2CH_2CH_2OH$ and $CH_2CH_2OCH_2CH_2OH$; and
a is 0, 1, 2, 3, 4, or 5.

In particular, in some embodiments, $Ar^1$ can be substituted or unsubstituted aryl. In particular, in some embodiments, the substituted or unsubstituted aryl can be substituted or unsubstituted phenyl. Exemplary embodiments in which $Ar^1$ is substituted or unsubstituted phenyl include, for example a compound represented by Formula I-1:

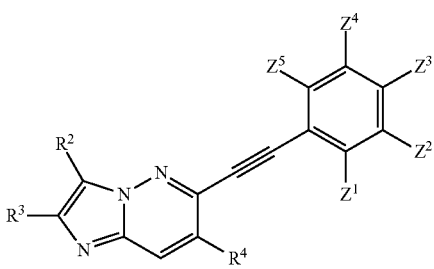

I-1 wherein one of $Z^1$ to $Z^5$ is —$X^1$—$R^1$, and the remaining $Z^1$ to $Z^5$ are independently selected from the group consisting of hydrogen and $C_1$ to $C_8$ alkyl; and $X^1$ and $R^1$ to $R^4$ are as defined herein.

In other embodiments, $Ar^1$ can be substituted or unsubstituted heteroaryl. In particular, in some embodiments, the substituted or unsubstituted heteroaryl can be substituted or unsubstituted pyridinyl. Exemplary embodiments in which Ar¹ is substituted or unsubstituted pyrdinyl include, for example, compounds represented by Formulas I-2, I-3, or I-4:

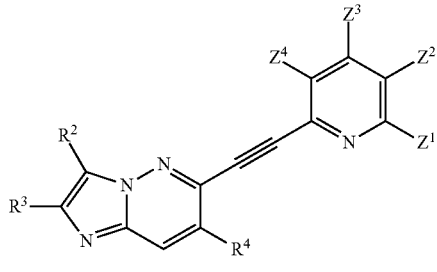

I-2

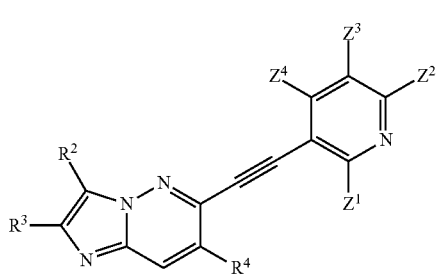

I-3

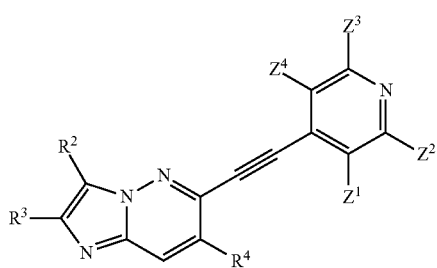

I-4 wherein one of Z¹ to Z⁴ is $\xi$—X¹—R¹, and the remaining Z¹ to Z⁴ are independently selected from the group consisting of hydrogen and C₁ to C₈ alkyl; and X¹ and R¹ to R⁴ are as defined herein.

In some embodiments, the substituted or unsubstituted heteroaryl can be substituted or unsubstituted pyrrolyl, substituted or unsubstituted thiophenyl, or substituted or unsubstituted furanyl. Exemplary embodiments in which Ar¹ is substituted or unsubstituted pyrrolyl, substituted or unsubstituted thiophenyl, or substituted or unsubstituted furanyl, include, for example, compounds represented by Formulas I-5 or I-6:

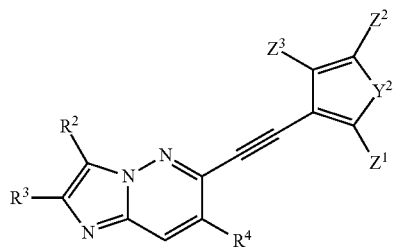

I-5

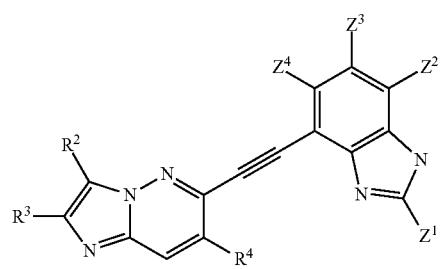

I-6 wherein Y² is selected from the group consisting of NR^a, S, and O; one of Z¹ to Z³ is $\xi$—X¹—R¹, and the remaining Z¹ to Z³ are independently selected from the group consisting of hydrogen and C₁ to C₈ alkyl; and X¹, R¹ to R⁴, and R^a are as defined herein.

In some embodiments, the substituted or unsubstituted heteroaryl can be substituted or unsubstituted benzo[d]imidazolyl. Exemplary embodiments in which Ar¹ is substituted or unsubstituted benzo[d]imidazolyl include, for example, compounds represented by Formulas I-7 and I-8:

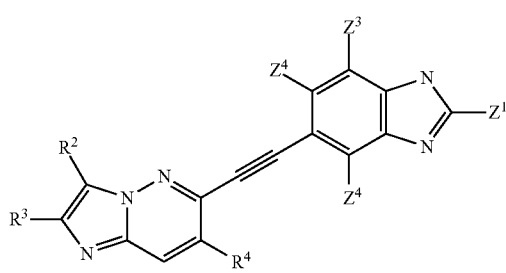

I-7

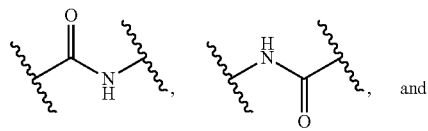

I-8 wherein one of Z¹ to Z⁴ is $\xi$—X¹—R¹, and the remaining Z¹ to Z⁴ are independently selected from the group consisting of hydrogen and C₁ to C₈ alkyl; and X¹ and R¹ to R⁴ are as defined herein.

In some embodiments, X¹ is selected from the group consisting of:

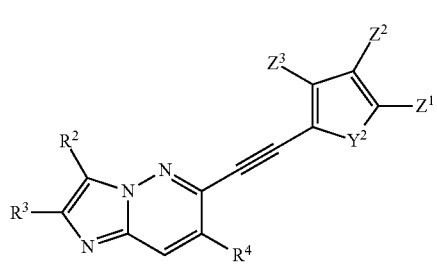

and

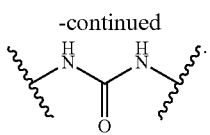

Exemplary embodiments with the $X^1$ groups indicated above include, for example, compounds represented by formulas I-9, I-10, and I-11:

I-9

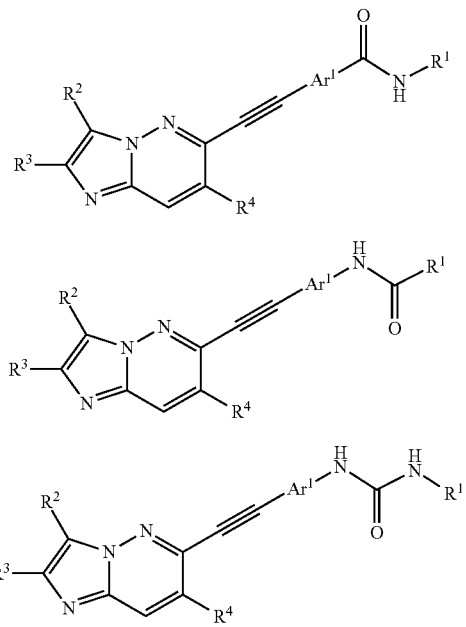

I-10

I-11 wherein $Ar^1$, $X^1$, and $R^1$ to $R^4$ are as defined herein.

In some embodiments, $X^1$ is selected from the group consisting of:

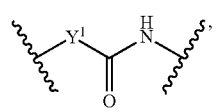 and 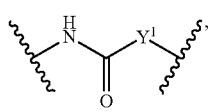

wherein $Y^1$ is selected from the group consisting of O, $CR^aR^b$, and $NR^c$, and wherein $R^a$ and $R^b$ are independently selected from the group consisting of hydrogen and $C_1$ to $C_8$ alkyl, and $R^c$ is $C_1$ to $C_8$ alkyl.

Exemplary embodiments with the $X^1$ groups indicated above include, for example, compounds represented by formulas I-12, I-13, I-14, I-15, I-16, and I-17:

I-12

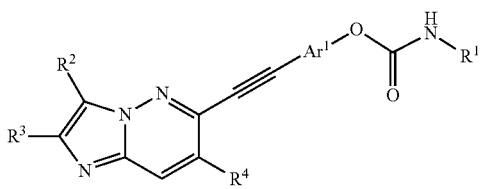

I-13

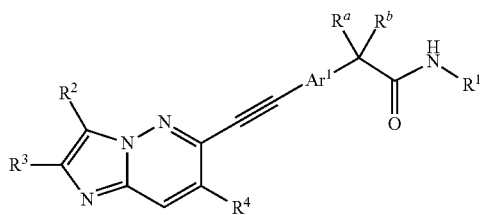

I-14

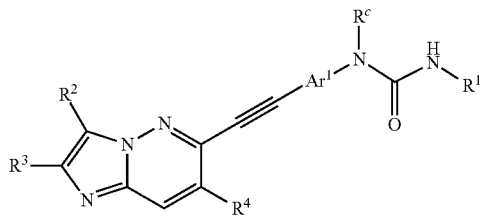

I-15

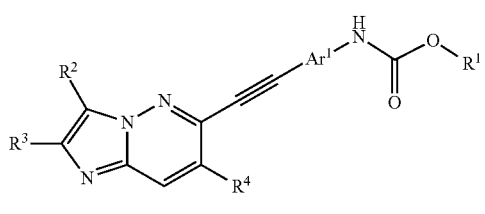

I-16

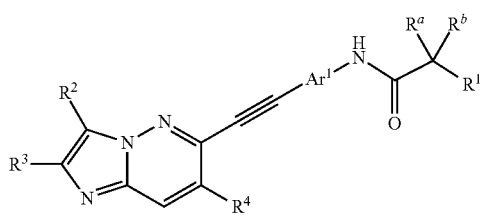

I-17

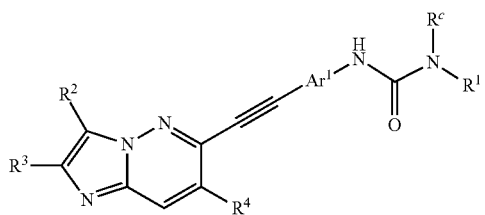

wherein $Ar^1$, $X^1$, $R^1$ to $R^4$, $R^a$, $R^b$, and $R^c$ are as defined herein.

In some embodiments, $R^1$ can be substituted or unsubstituted aryl. In particular, in some embodiments, the substituted or unsubstituted aryl can be substituted or unsubstituted phenyl. Exemplary embodiments in which $R^1$ is substituted or unsubstituted phenyl include, for example a compound represented by Formula I-18:

I-18

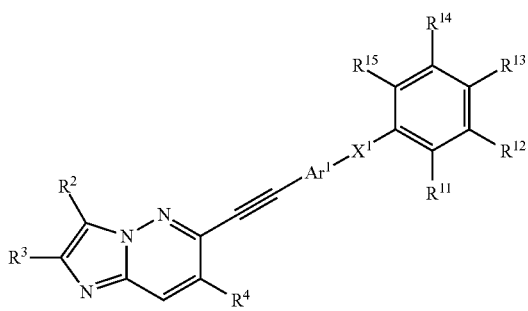

wherein $R^{11}$ to $R^{15}$ are independently selected from the group consisting of hydrogen, methyl, trifluoromethyl, $OR^{16}$, $N(R^{17})R^{18}$, and halogen; $R^{16}$ to $R^{18}$ are independently $C_1$ to $C_8$ alkyl; and $Ar^1$, $X^1$, and $R^2$ to $R^4$ are as defined herein.

In other embodiments, $R^1$ can be substituted or unsubstituted heteroaryl. In particular, in some embodiments, $R^1$ can be substituted or unsubstituted pyridyl. Exemplary embodiments in which $R^1$ is substituted or unsubstituted pyridyl, include, for example, compounds represented by Formulas I-19, I-20, and I-21:

I-19

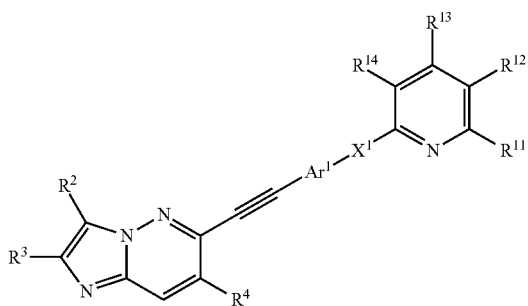

I-20

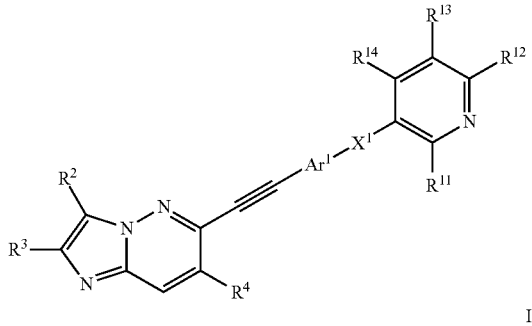

I-21

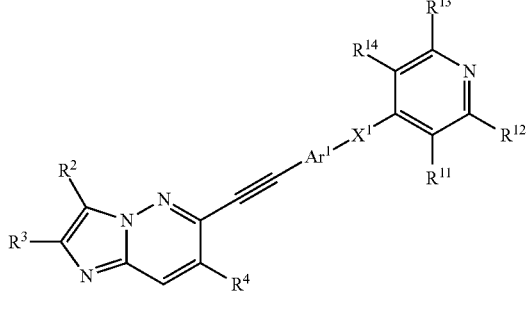

wherein $R^{11}$ to $R^{14}$ are independently selected from the group consisting of hydrogen, methyl, trifluoromethyl, $OR^{16}$, $N(R^{17})R^{18}$, and halogen; $R^{16}$ to $R^{18}$ are independently $C_1$ to $C_8$ alkyl; and $Ar^1$, $X^1$, and $R^2$ to $R^4$ are as defined herein.

In some embodiments, $R^3$ is selected from the group consisting of hydrogen, $C_1$ to $C_8$ alkyl, $(CR^5R^6)_aC(O)OR^7$, $(CR^5R^6)_aOR^7$, $(CR^5R^6)_aN(R^{10})C(O)R^7$, $(CR^5R^6)_aC(O)N(R^8)R^9$, $(CR^5R^6)_aN(R^{10})C(O)OR^7$, $(CR^5R^6)_aN(R^{10})C(O)N(R^8)R^9$, and $(CR^5R^6)_aN(R^8)R^9$, wherein:

$R^5$ is selected from the group consisting of hydrogen, $C_1$ to $C_8$ alkyl, fluoro, hydroxy, hydroxymethyl, $C(O)CH_3$, $CH_2CH_2OH$, $CH_2CH_2CH_2OH$ and $CH_2CH_2OCH_2CH_2OH$;

$R^6$ is selected from the group consisting of hydrogen, $C_1$ to $C_8$ alkyl, hydroxy, and fluoro;

$R^7$ is selected from the group consisting of hydrogen, $C_1$ to $C_8$ alkyl, substituted or unsubstituted aryl, substituted or unsubstituted heteroaryl, halogen, hydroxy, hydroxymethyl, $COCH_3$, $CH_2CH_2OH$ and $CH_2CH_2CH_2OH$;

$R^8$ is selected from the group consisting of hydrogen, $C_1$ to $C_8$ alkyl, substituted or unsubstituted aryl, substituted or unsubstituted heteroaryl, halogen, hydroxy, hydroxymethyl, $COCH_3$, $CH_2CH_2OH$ and $CH_2CH_2CH_2OH$; or $R^8$ together with $R^9$ forms a substituted or unsubstituted heterocyclic ring;

$R^9$ is selected from the group consisting of hydrogen, $C_1$ to $C_8$ alkyl, substituted or unsubstituted aryl, substituted or unsubstituted heteroaryl, halogen, hydroxy, hydroxymethyl, $COCH_3$, $CH_2CH_2OH$ and $CH_2CH_2CH_2OH$; or $R^9$ together with $R^8$ forms a substituted or unsubstituted heterocyclic ring;

$R^{10}$ is selected from the group consisting of hydrogen, $C_1$ to $C_8$ alkyl, fluoro, hydroxy, hydroxymethyl, $C(O)CH_3$, $CH_2CH_2OH$, $CH_2CH_2CH_2OH$ and $CH_2CH_2OCH_2CH_2OH$; and a is 0, 1, 2, 3, 4, or 5.

Exemplary embodiments in which $R^3$ is selected from the group consisting of $(CR^5R^6)_aC(O)OR^7$, $(CR^5R^6)_aOR^7$, $(CR^5R^6)_aN(R^{10})C(O)R^7$, $(CR^5R^6)_aC(O)N(R^8)R^9$, $(CR^5R^6)_aN(R^{10})C(O)OR^7$, $(CR^5R^6)_aN(R^{10})C(O)N(R^8)R^9$, and $(CR^5R^6)_aN(R^8)R^9$, include, for example, compounds represented by Formulas I-22, I-23, I-24, I-25, I-26, I-27, and I-28:

I-22

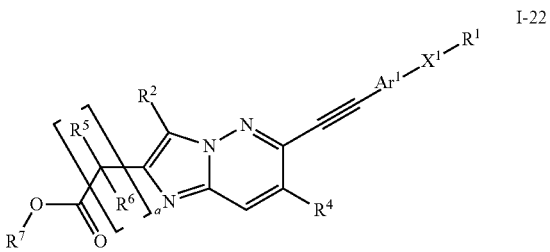

I-23

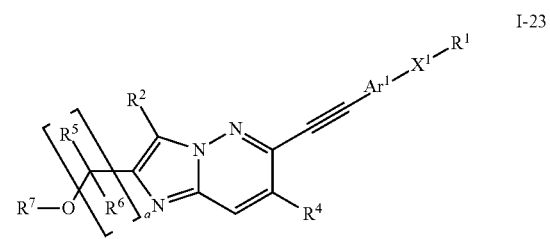

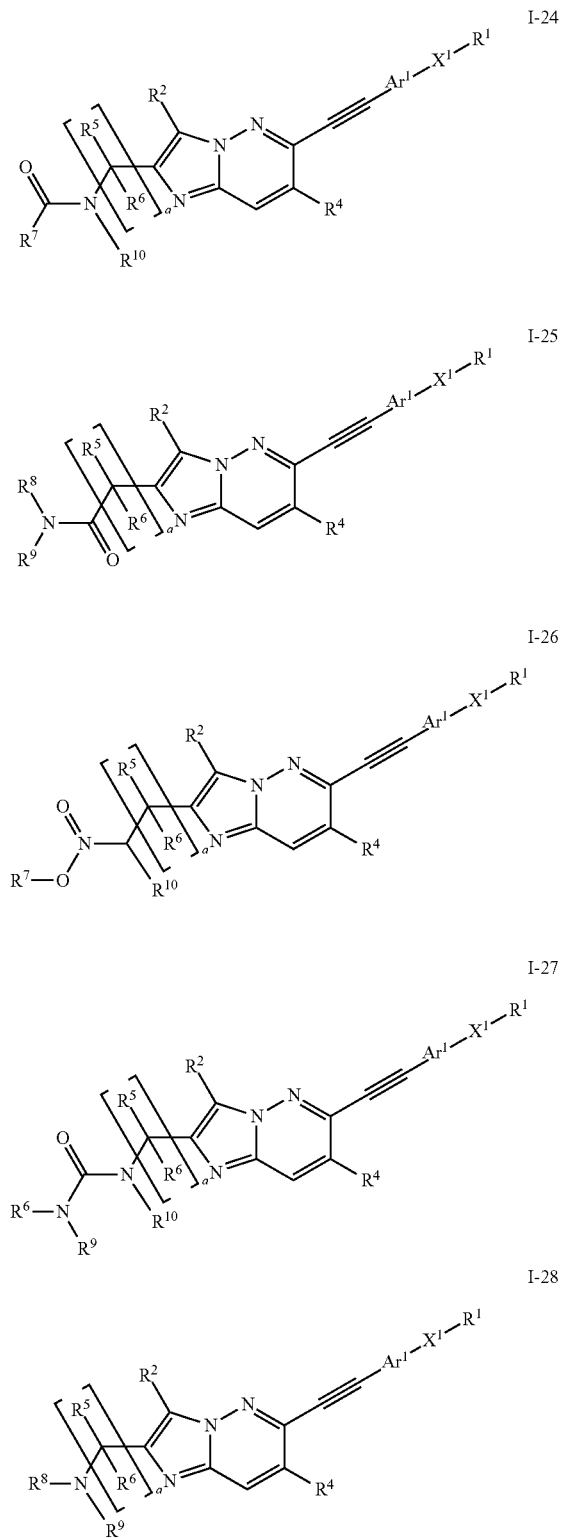

wherein $Ar^1$, $X^1$, $R^1$, $R^2$, and $R^4$ to $R^{10}$ are as defined herein.

In some embodiments, $R^3$ is selected from the group consisting of $(CR^5R^6)_aC(O)N(R^8)R^9$, $(CR^5R^6)_aN(R^{10})C(O)N(R^8)R^9$, and $(CR^5R^6)_aN(R^8)R^9$, wherein $R^5$, $R^6$, $R^{10}$, and a are as defined herein, and wherein $R^8$ and $R^9$ together with each other form a ring. Exemplary embodiments wherein $R^8$ and $R^9$ together with each other form a ring include, for example, compounds represented by Formulas I-29, I-30, I-31, I-32, I-33, I-34, I-35, I-36, I-37, I-38, I-39, and I-40:

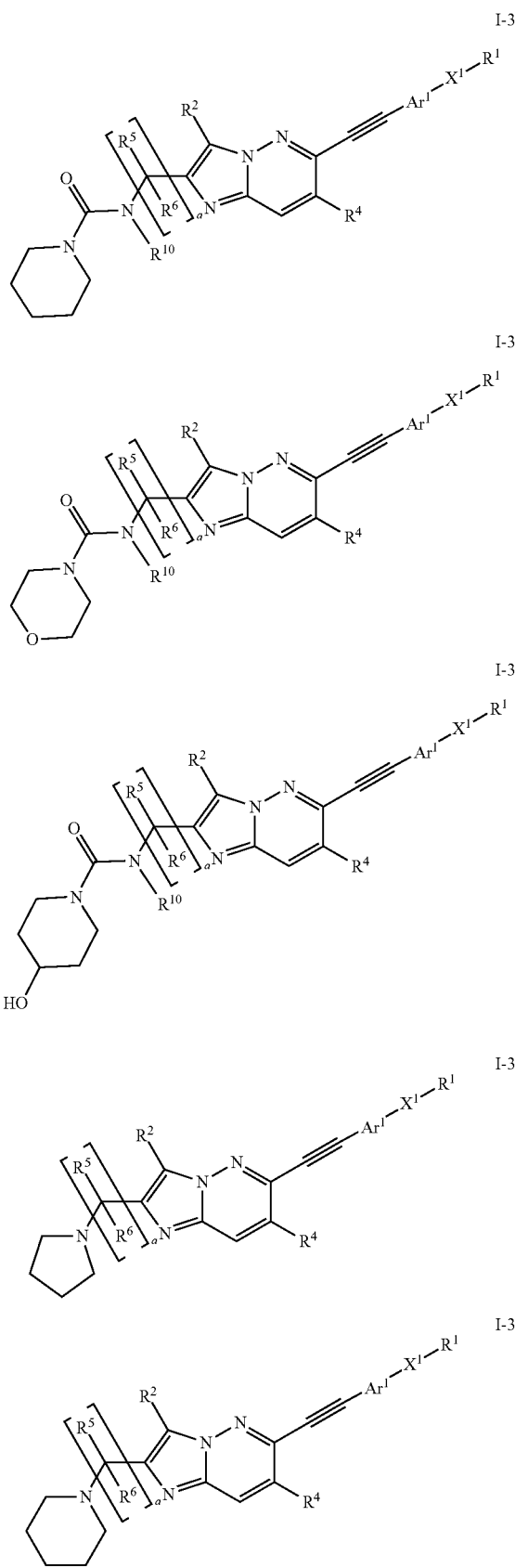
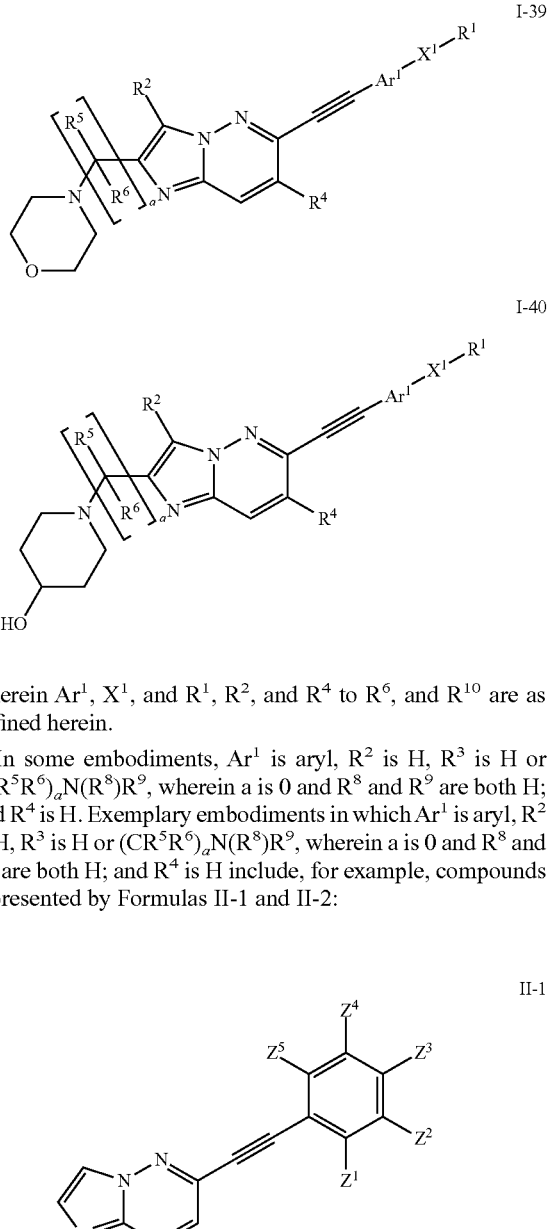

wherein $Ar^1$, $X^1$, and $R^1$, $R^2$, and $R^4$ to $R^6$, and $R^{10}$ are as defined herein.

In some embodiments, $Ar^1$ is aryl, $R^2$ is H, $R^3$ is H or $(CR^5R^6)_aN(R^8)R^9$, wherein a is 0 and $R^8$ and $R^9$ are both H; and $R^4$ is H. Exemplary embodiments in which $Ar^1$ is aryl, $R^2$ is H, $R^3$ is H or $(CR^5R^6)_aN(R^8)R^9$, wherein a is 0 and $R^8$ and $R^9$ are both H; and $R^4$ is H include, for example, compounds represented by Formulas II-1 and II-2:

wherein one of $Z^1$ to $Z^7$ is —$X^1$—$R^1$, and the remaining $Z^1$ to $Z^7$ are independently selected from the group consisting of hydrogen and $C_1$ to $C_8$ alkyl; and $X^1$ and $R^1$ are as defined herein. In particular, in some embodiments of Formulas II-1 and II-2, $X^1$ can be:

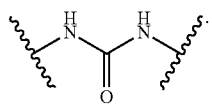

In particular, in some embodiments of Formulas II-1 and II-2 wherein $X^1$ is

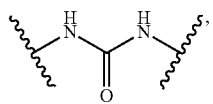

$R^1$ can be:

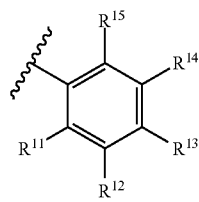

wherein $R^{11}$ to $R^{15}$ are independently selected from the group consisting of hydrogen, methyl, trifluoromethyl, $OR^{16}$, $N(R^{17})R^{18}$, and halogen, wherein $R^{16}$ to $R^{18}$ are independently $C_1$ to $C_8$ alkyl.

In particular, in some embodiments, compounds as described herein are represented by Formula III:

III

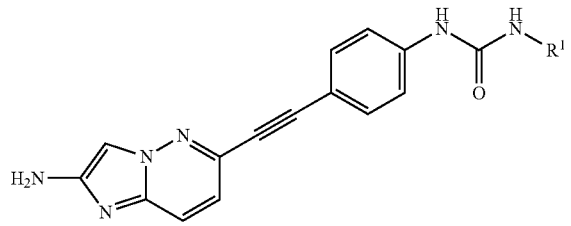

wherein $R^1$ as is defined herein.

In some embodiments of Formula III, $R^1$ is substituted or unsubstituted aryl. Exemplary embodiments in which $R^1$ is aryl include, for example, a compound according to Formula IV:

IV

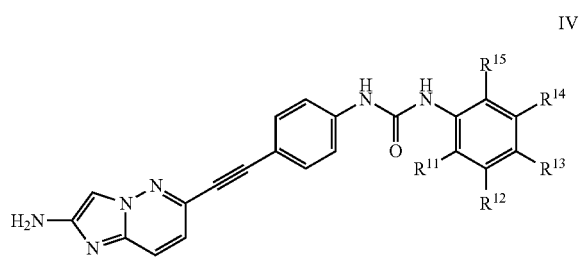

wherein $R^{11}$ to $R^{15}$ are independently selected from the group consisting of hydrogen, methyl, trifluoromethyl, $OR^{16}$, $N(R^{17})R^{18}$, and halogen, wherein $R^{16}$ to $R^{18}$ are independently $C_1$ to $C_8$ alkyl.

In particular, in some embodiments, compounds as described herein are represented by Formula V:

V

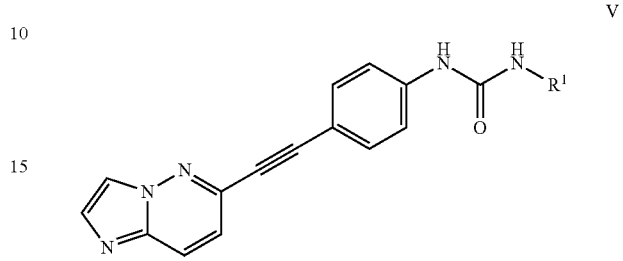

wherein $R^1$ as is defined herein.

In some embodiments of Formula V, $R^1$ is substituted or unsubstituted aryl. Exemplary embodiments in which $R^1$ is aryl include, for example, a compound according to Formula VI:

VI

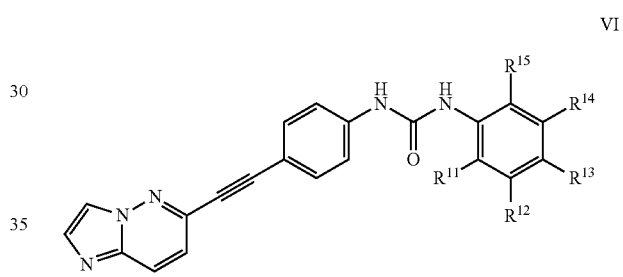

wherein $R^{11}$ to $R^{15}$ are independently selected from the group consisting of hydrogen, methyl, trifluoromethyl, $OR^{16}$, $N(R^{17})R^{18}$, and halogen, wherein $R^{16}$ to $R^{18}$ are independently $C_1$ to $C_8$ alkyl.

In particular, in some embodiments, the compound of Formula I is a compound selected from the group consisting of 1-{4-[(2-aminoimidazo[1,2-b]pyridazin-6-yl)ethynyl]phenyl}-3-(3-methylphenyl)urea; 1-[4-(imidazo[1,2-b]pyridazin-6-ylethynyl)phenyl]-3-[3-(trifluoromethyl)phenyl]urea; 1-[4-(imidazo[1,2-b]pyridazin-6-ylethynyl)phenyl]-3-(3-methylphenyl)urea; 1-{4-[(2-aminoimidazo[1,2-b]pyridazin-6-yl)ethynyl]phenyl}-3-[2-fluoro-5-(trifluoromethyl)phenyl]urea; 1-(3-chloro-4-fluorophenyl)-3-[4-(imidazo[1,2-b]pyridazin-6-ylethynyl)phenyl]urea; 1-(2-fluoro-5-methylphenyl)-3-[4-(imidazo[1,2-b]pyridazin-6-ylethynyl)phenyl]urea; 1-[4-chloro-3-(trifluoromethyl)phenyl]-3-[4-(imidazo[1,2-b]pyridazin-6-ylethynyl)phenyl]urea; 1-[4-(imidazo[1,2-b]pyridazin-6-ylethynyl)phenyl]-3-phenylurea; 1-[2-fluoro-5-(trifluoromethyl)phenyl]-3-[4-(imidazo[1,2-b]pyridazin-6-ylethynyl)phenyl]urea; 1-[2-fluoro-5-(trifluoromethyl)phenyl]-3-[4-({2-[({[2-fluoro-5-(trifluoromethyl)phenyl]amino}carbonyl)amino]imidazo[1,2-b]pyridazin-6-yl}ethynyl)phenyl]urea; N-(6-{[4-({[(3-methylphenyl)amino]carbonyl}amino)phenyl]ethynyl}imidazo[1,2-b]pyridazin-2-yl)acetamide; N-(6-{[4-({[(3-methylphenyl)amino]carbonyl}amino)phenyl]ethynyl}imidazo[1,2-b]pyridazin-2-yl)cyclopropanecarboxamide; 1-[4-(imidazo[1,2-b]pyridazin-6-ylethynyl)phenyl]-3-(4-methylphenyl)urea; 1-{6-[(4- aminophenyl)ethynyl]imidazo[1,2-b]pyridazin-2-yl}-3-(3-chloro-4-fluorophenyl)urea; 1-(3-chloro-4-fluorophenyl)-3-(4-{[2-({[(3-chloro-4-fluorophenyl)amino]carbonyl}amino)imidazo[1,2-b]pyridazin-6-yl]ethynyl}phenyl)urea; N-{4-[(2-aminoimidazo[1,2-b]pyridazin-6-yl)ethynyl]phenyl}benzamide; N-{4-[(2-aminoimidazo[1,2-b]pyridazin-6-yl)ethynyl]phenyl}-2-fluoro-5-methylbenzamide; N-{3-[(2-aminoimidazo[1,2-b]pyridazin-6-yl)ethynyl]phenyl}-2-fluoro-5-methylbenzamide; N-[3-(imidazo[1,2-b]pyridazin-6-ylethynyl)phenyl]-3-(trifluoromethyl)benzamide; N-[3-(imidazo[1,2-b]pyridazin-6-ylethynyl)phenyl]-3-methylbenzamide; 3-chloro-4-fluoro-N-[3-(imidazo[1,2-b]pyridazin-6-ylethynyl)phenyl]benzamide; N-[3-(imidazo[1,2-b]pyridazin-6-ylethynyl)phenyl]-1-benzofuran-2-carboxamide; 2-fluoro-N-[3-(imidazo[1,2-b]pyridazin-6-ylethynyl)phenyl]-5-methylbenzamide; N-[3-(imidazo[1,2-b]pyridazin-6-ylethynyl)phenyl]benzamide; N-[3-(imidazo[1,2-b]pyridazin-6-ylethynyl)phenyl]-4-methylbenzamide; 1-(2-fluoro-5-methylphenyl)-3-[3-(imidazo[1,2-b]pyridazin-6-ylethynyl)phenyl]urea; and 1-(2-fluoro-5-methylphenyl)-3-[2-(imidazo[1,2-b]pyridazin-6-ylethynyl)phenyl]urea.

In some embodiments, compounds of the present invention are represented by Formula VII:

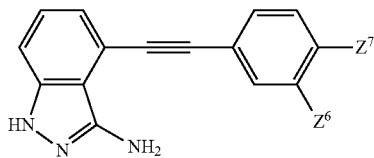

VII or a pharmaceutically acceptable salt thereof, wherein one of $Z^6$ and $Z^7$ is independently hydrogen and the other is independently:

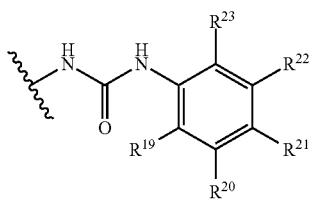

wherein $R^{19}$ to $R^{23}$ are independently selected from the group consisting of hydrogen, methyl, trifluoromethyl, $OR^{24}$, $N(R^{25})R^{26}$, and halogen; $R^{24}$ to $R^{26}$ are independently $C_1$ to $C_8$ alkyl.

Exemplary compounds of Formula VIII wherein one of $Z^6$ and $Z^7$ is independently hydrogen and the other is independently

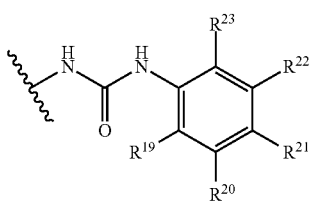

include, for example, compounds represented by Formulas VII-1 and VII-2:

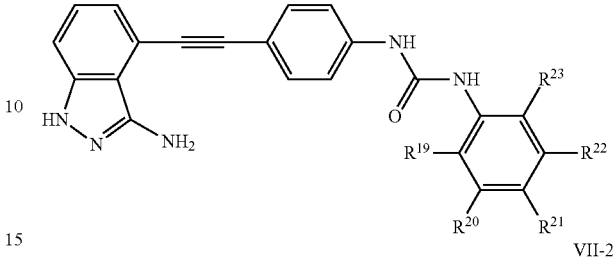

VII-1

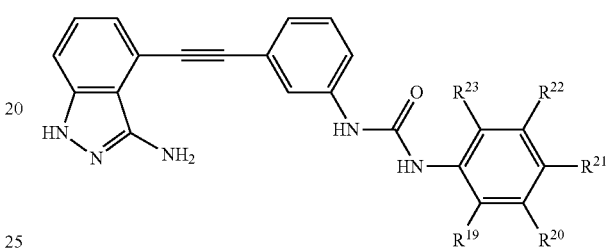

VII-2 wherein $R^{19}$ to $R^{23}$ are as defined herein.

In particular, in some embodiments, the compound of Formula VII is a compound selected from the group consisting of: 1-{3-[(3-amino-1H-indazol-4-yl)ethynyl]phenyl}-3-(2-fluoro-5-methylphenyl)urea; 1-{3-[(3-amino-1H-indazol-4-yl)ethynyl]phenyl}-3-phenylurea; and 1-{4-[(3-amino-1H-indazol-4-yl)ethynyl]phenyl}-3-(2-fluoro-5-methylphenyl) urea.

In some embodiments, compounds described herein are useful as protein kinase inhibitors. As such, compounds described herein will be useful for treating diseases related to protein kinase signal transduction, for example, cancer, blood vessel proliferative disorders, fibrotic disorders, and neurodegenerative diseases. In particular, the compounds of the present invention are useful for treatment of mesangial cell proliferative disorders and metabolic diseases, lung carcinomas, breast carcinomas, Non Hodgkin's lymphomas, ovarian carcinoma, pancreatic cancer, malignant pleural mesothelioma, melanoma, arthritis, restenosis, hepatic cirrhosis, atherosclerosis, psoriasis, rosacea, diabetic mellitus, wound healing, inflammation and neurodegenerative diseases and also ophthalmic diseases, i.e. diabetic retinopathy, retinopathy of prematurity, macular edema, retinal vein occlusion, exudative or neovascular age-related macular degeneration, high-risk eyes (i.e. fellow eyes have neovascular age-related macular degeneration) with dry age-related macular degeneration, neovascular disease associated with retinal vein occlusion, neovascular disease (including choroidal neovascularization) associated with the following: pathologic myopia, pseudoxanthoma elasticum, optic nerve drusen, traumatic choroidal rupture, atrophic macular degeneration, geographic atrophy, central serous retinopathy, cystoid macular edema, diabetic retinopathy, proliferative diabetic retinopathy, diabetic macular edema, rubeosis iridis, retinopathy of prematurity, central and branch retinal vein occlusions, inflammatory/infectious retinal, neovascularization/edema, corneal neovascularization, hyperemia related to an actively inflamed pterygia, recurrent pterygia following excisional surgery, post-excision, progressive pterygia approaching the visual axis, prophylactic therapy to prevent recurrent pterygia, of post-excision, progressive pterygia approaching the visual axis, chronic low grade hyperemia associated with pterygia, neovascular glaucoma, iris neovascularization, idiopathic etiologies, presumed ocular histoplasmosis syndrome, retinopathy of prematurity, chronic allergic conjunctivitis, ocular rosacea, blepharoconjunctivitis, recurrent episcleritis, keratoconjunctivitis sicca, ocular graft vs host disease, etc.

Some compounds described herein and some of their intermediates in their syntheses have at least one asymmetric center in their structure. This asymmetric center can be present in an R or S configuration, said R and S notation is used in correspondence with the rules described in *Pure Applied Chem.* 1976, 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

In some embodiments, the acid addition salt form of compounds described herein that occur in their free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic and the like (*Handbook of Pharmaceutical Salts*, P. Heinrich Stahl & Camille G. Wermuth (Eds), Verlag; *Helvetica Chimica Acta-Zürich,* 2002, 329-345).

In some embodiments, the base addition salt form of compounds described herein that occur in their acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-Arginine, ethanolamine, betaine, benzathine, morpholine and the like. (*Handbook of Pharmaceutical Salts*, P. Heinrich Stahl & Camille G. Wermuth (Eds), Verlag; *Helvetica Chimica Acta-Zürich,* 2002, 329-345).

In some embodiments, compounds described herein and their salts can be in the form of a solvate, which is included within the scope of the present invention. Such solvates include for example hydrates, alcoholates and the like.

With respect to the present invention reference to a compound or compounds described herein, is intended to encompass that compound in each of its possible isomeric forms and mixtures thereof unless the particular isomeric form is referred to specifically.

In some embodiments, compounds described herein can exist in different polymorphic forms. Although not explicitly indicated in the above formula, such forms are intended to be included within the scope of the present invention.

The actual amount of the compound to be administered in any given case will be determined by a physician taking into account the relevant circumstances, such as the severity of the condition, the age and weight of the patient, the patient's general physical condition, the cause of the condition, and the route of administration.

The patient can be administered the compound orally in any acceptable form, such as a tablet, liquid, capsule, powder and others identifiable to a skilled person, or other routes can be desirable or necessary, particularly if the patient suffers from nausea. Such other routes can include, for example, transdermal, parenteral, subcutaneous, intranasal, via an implant stent, intrathecal, intravitreal, topical to the eye, back to the eye, intramuscular, intravenous, intrarectal modes of delivery, and others identifiable to a skilled person. Additionally, the formulations can be designed to delay release of the active compound over a given period of time, or to carefully control the amount of drug released at a given time during the course of therapy.

In another embodiment of the invention, there are provided pharmaceutical compositions including at least one compound described herein in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the compounds described herein can be used in the form of a solid, a solution, an emulsion, a dispersion, a patch, a micelle, a liposome, and others identifiable to a skilled person, wherein the resulting composition contains one or more compounds of the present invention, as an active ingredient, in admixture with an organic or inorganic carrier or excipient suitable for enteral or parenteral applications. Compounds described herein can be combined, for example, with the usual non-toxic, pharmaceutically acceptable carriers for tablets, pellets, capsules, suppositories, solutions, emulsions, suspensions, and any other form suitable for use identifiable to a skilled person. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers identifiable to a skilled person suitable for use in manufacturing preparations, in solid, semisolid, or liquid form. In addition auxiliary agents, stabilizing agents, thickening agents, coloring agents, and perfumes can be used. Compounds described herein are included in the pharmaceutical composition in an amount sufficient to produce the desired effect upon the process or disease condition.

Pharmaceutical compositions containing compounds described herein can be in a form suitable for oral use, for example, as tablets, troches, lozenges, aqueous or oily suspensions, dispersible powders or granules, emulsions, hard or soft capsules, or syrups or elixirs, as well as others identifiable to a skilled person. Compositions intended for oral use can be prepared according to any method known in the art, and others identifiable to a skilled person, for the manufacture of pharmaceutical compositions and such compositions can contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients can also be manufactured by known methods. The excipients used can be, for example, (1) inert diluents such as calcium carbonate, lactose, calcium phosphate or sodium phosphate, or others identifiable to a skilled person; (2) granulating and disintegrating agents such as corn starch, potato starch or alginic acid, or others identifiable to a skilled person; (3) binding agents such as gum tragacanth, corn starch, gelatin or acacia, or others identifiable to a skilled person, and (4) lubricating agents such as magnesium stearate, stearic acid or talc, or others identifiable to a skilled person. The tablets can be uncoated or they can be coated by known techniques identifiable to a skilled person to delay disintegration and absorption in the gastrointestinal tract and thereby provide a sustained action over a longer period. For example, a time delay material such as glyceryl monostearate or glyceryl distearate can be employed.

In some cases, formulations for oral use can be in the form of hard gelatin capsules wherein the invention compounds are mixed with an inert solid diluent, for example, calcium carbonate, calcium phosphate or kaolin, or others identifiable to a skilled person. Formulations can also be in the form of soft gelatin capsules wherein the invention compounds are mixed with water or an oil medium, for example, peanut oil, liquid paraffin or olive oil, or others identifiable to a skilled person.

The pharmaceutical compositions can be in the form of a sterile injectable suspension. This suspension can be formulated according to known methods identifiable to a skilled person using suitable dispersing or wetting agents and suspending agents. The sterile injectable preparation can also be a sterile injectable solution or suspension in a non-toxic parenterally acceptable diluent or solvent, for example, as a solution in 1,3-butanediol, or other non-toxic parenterally acceptable diluents or solvents identifiable to a skilled person. Sterile, fixed oils are conventionally employed as a solvent or suspending medium. For this purpose, a bland fixed oil can be employed including synthetic mono- or diglycerides, fatty acids (including oleic acid), naturally occurring vegetable oils like sesame oil, coconut oil, peanut oil, cottonseed oil, and others identifiable to a skilled person, or synthetic fatty vehicles like ethyl oleate and others identifiable to a skilled person. Buffers, preservatives, antioxidants, and others identifiable to a skilled person can be incorporated as required.

Pharmaceutical compositions containing invention compounds can be in a form suitable for topical use, for example, as oily suspensions, as solutions or suspensions in aqueous liquids or nonaqueous liquids, or as oil-in-water or water-in-oil liquid emulsions. Pharmaceutical compositions can be prepared by combining a therapeutically effective amount of at least one compound according to the present invention, or a pharmaceutically acceptable salt thereof, as an active ingredient with conventional ophthalmically acceptable pharmaceutical excipients and by preparation of unit dosage suitable for topical ocular use. The therapeutically efficient amount typically is between about 0.0001 and about 5% (w/v), or about 0.001 to about 2.0% (w/v) in liquid formulations. Other therapeutically efficient amounts will be apparent to a skilled person upon a reading of the present disclosure.

For ophthalmic application, solutions can be prepared using a physiological saline solution as a major vehicle. The pH of such ophthalmic solutions can be maintained between 4.5 and 8.0 with an appropriate buffer system identifiable to a skilled person, for example at a neutral pH. The formulations can also contain conventional pharmaceutically acceptable preservatives, stabilizers and surfactants. Exemplary preservatives that can be used in the pharmaceutical compositions described herein include, but are not limited to, benzalkonium chloride, chlorobutanol, thimerosal, phenylmercuric acetate, phenylmercuric nitrate, and others identifiable to a skilled person. An exemplary surfactant is, for example, Tween 80. Likewise, various vehicles can be used in the ophthalmic preparations described herein. These vehicles can include, but are not limited to, polyvinyl alcohol, povidone, hydroxypropyl methyl cellulose, poloxamers, carboxymethyl cellulose, hydroxyethyl cellulose cyclodextrin, purified water, and others identifiable to a skilled person.

Tonicity adjustors can be added as needed or convenient. They include, but are not limited to, salts (for example sodium chloride, potassium chloride, and others identifiable to a skilled person), mannitol and glycerin, or any other suitable ophthalmically acceptable tonicity adjustor identifiable to a skilled person.

Various buffers and means for adjusting pH can be used so long as the resulting preparation is ophthalmically acceptable. Accordingly, buffers can include acetate buffers, citrate buffers, phosphate buffers, borate buffers, and others identifiable to a skilled person. Acids or bases can be used to adjust the pH of these formulations as needed.

In a similar manner an ophthalmically acceptable antioxidant for use in the compositions described herein includes, but is not limited to, sodium metabisulfite, sodium thiosulfate, acetylcysteine, butylated hydroxyanisole, butylated hydroxytoluene, and others identifiable to a skilled person.

Other excipient components which can be included in the ophthalmic preparations are chelating agents. An exemplary chelating agent is edentate disodium, although other chelating agents identifiable to a skilled person can also be used in place of or in conjunction with it.

The ingredients are usually used in the following amounts:
Ingredient Amount (% w/v)
active ingredient about 0.001 to 5
preservative 0 to 0.10
vehicle 0 to 40
tonicity adjustor 0 to 10
buffer 0.01 to 10
pH adjustor q.s. pH 4.5 to 7.8
antioxidant as needed
surfactant as needed
purified water to make 100%

The actual dose of the active compounds of the present invention depends on the specific compound, and on the condition to be treated; the selection of the appropriate dose is well within the knowledge of the skilled artisan.

The ophthalmic formulations of the present invention can be packaged in forms suitable for metered application, such as in containers equipped with a dropper, to facilitate application to the eye. Containers suitable for dropwise application can be made of suitable inert, non-toxic plastic material, and can contain between about 0.5 and about 15 ml solution. One package can contain one or more unit doses. Foe example, preservative-free solutions can be often formulated in non-resealable containers containing up to about ten, or up to about five units doses, where a typical unit dose is from one to about 8 drops, or one to about 3 drops. The volume of one drop usually is about 20-35 µl.

The pharmaceutical compositions can be in the form of a sterile injectable suspension. This suspension can be formulated according to known methods using suitable dispersing or wetting agents and suspending agents. The sterile injectable preparation can also be a sterile injectable solution or suspension in a non-toxic parenterally-acceptable diluent or solvent, for example, as a solution in 1,3-butanediol. Sterile, fixed oils can be employed as a solvent or suspending medium. For this purpose a bland fixed oil can be employed including synthetic mono- or diglycerides, fatty acids (including oleic acid), naturally occurring vegetable oils like sesame oil, coconut oil, peanut oil, cottonseed oil, and others identifiable to a skilled person, or synthetic fatty vehicles like ethyl oleate and others identifiable to a skilled person. Buffers, preservatives, antioxidants, and others identifiable to a skilled person can be incorporated as required.

The compounds of the invention can also be administered in the form of suppositories for rectal administration of the drug. These compositions can be prepared by mixing the invention compounds with a suitable non-irritating excipient, such as, for example, cocoa butter, synthetic glyceride esters of polyethylene glycols, which are solid at ordinary temperatures, but liquefy and/or dissolve in the rectal cavity to release the drug.

Since individual subjects can present a wide variation in severity of symptoms and each drug has its unique therapeutic characteristics, the precise mode of administration and dosage employed for each subject is left to the discretion of the practitioner.

The present invention is further directed to pharmaceutical compositions comprising a pharmaceutically effective amount of one or more of the above-described compounds and a pharmaceutically acceptable carrier or excipient, wherein said compositions are effective for treating the above diseases and conditions; especially ophthalmic diseases and conditions. Such a composition is believed to modulate signal transduction by a tyrosine kinase, either by inhibition of catalytic activity, affinity to ATP or ability to interact with a substrate.

More particularly, the compositions of the present invention can be included in methods for treating diseases comprising proliferation, fibrotic or metabolic disorders, for example cancer, fibrosis, psoriasis, rosacea, atherosclerosis, arthritis, and other disorders related to abnormal vasculogenesis and/or angiogenesis, such as exudative age related macular degeneration and diabetic retinopathy.

The present invention concerns also processes for preparing the compounds described herein. In particular, the compounds described herein can be prepared analogously to conventional methods as understood by the person skilled in the art of synthetic organic chemistry. Synthetic Schemes 1 to 9 set forth below, illustrates how the compounds according to the invention can be made.

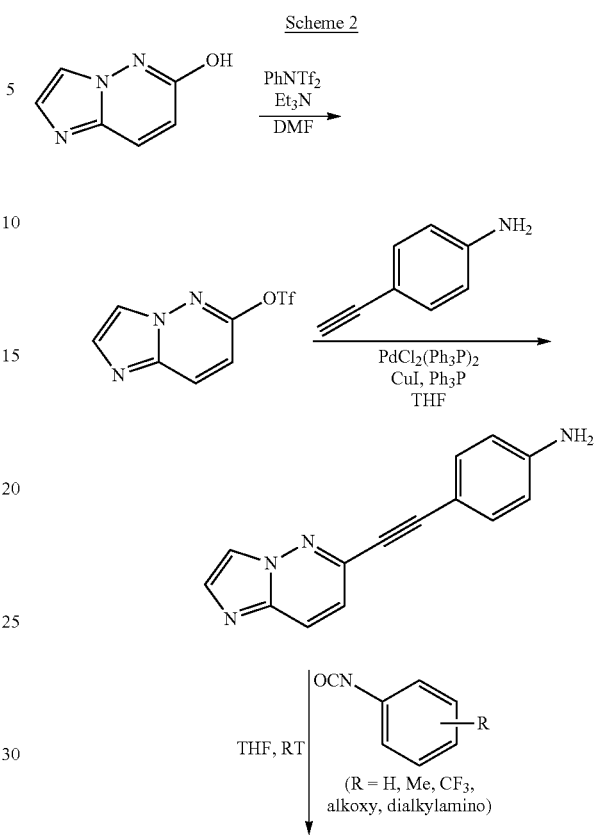

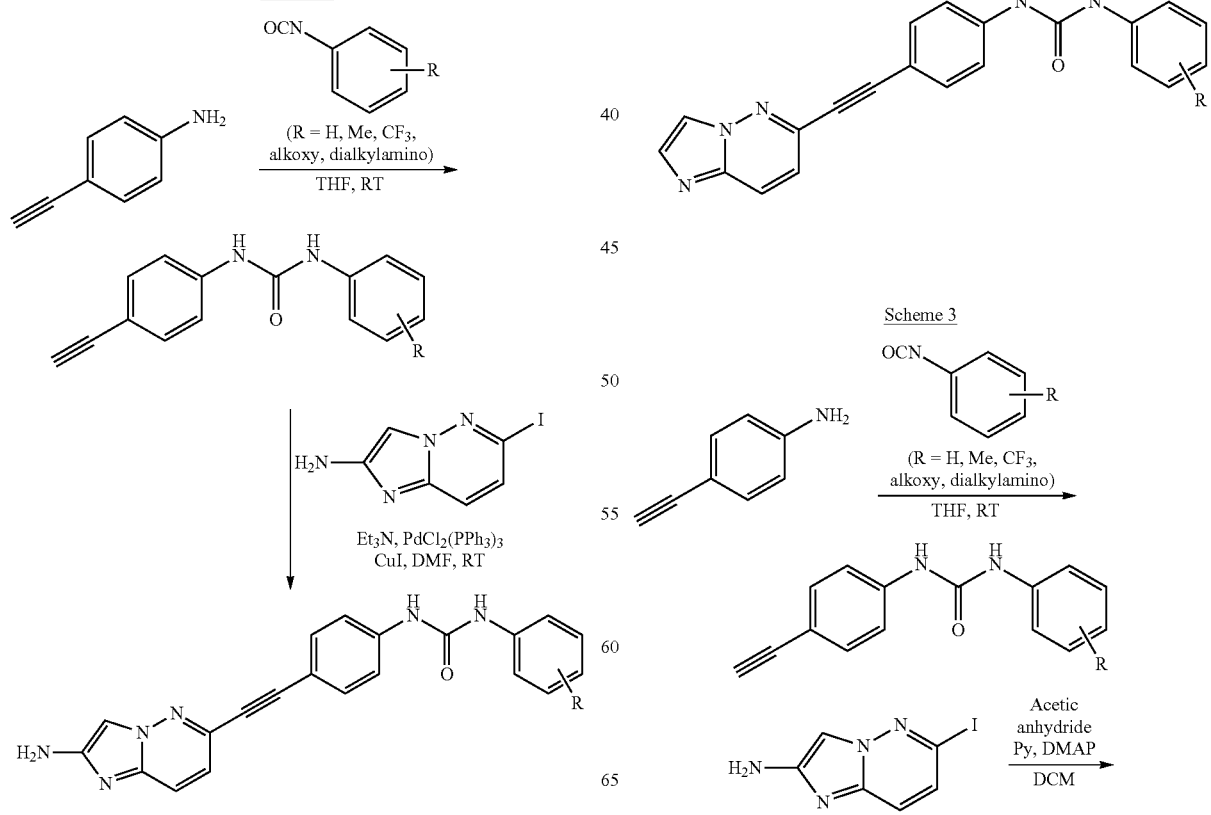

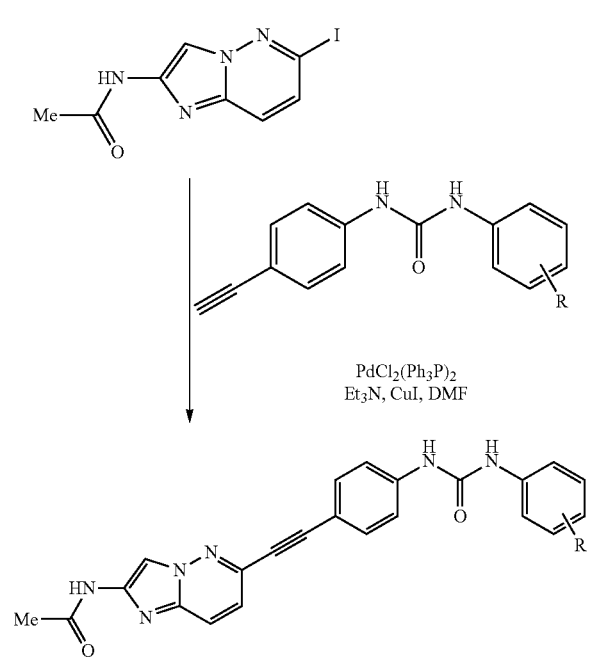
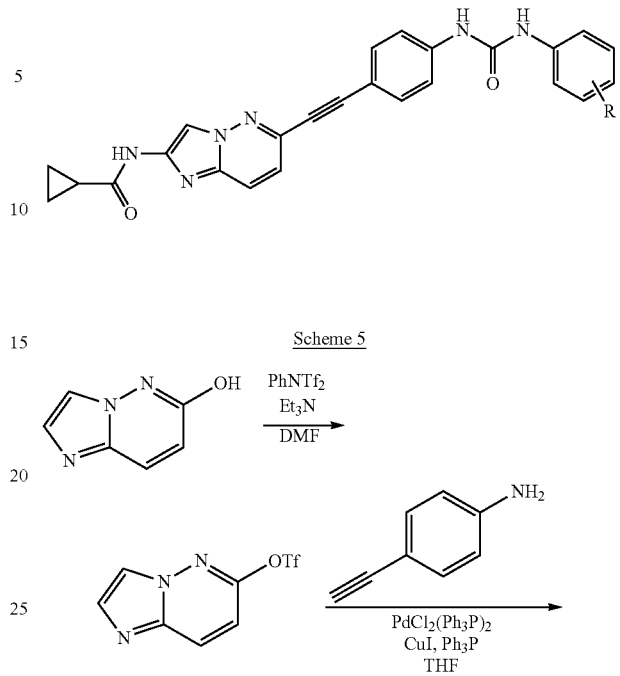
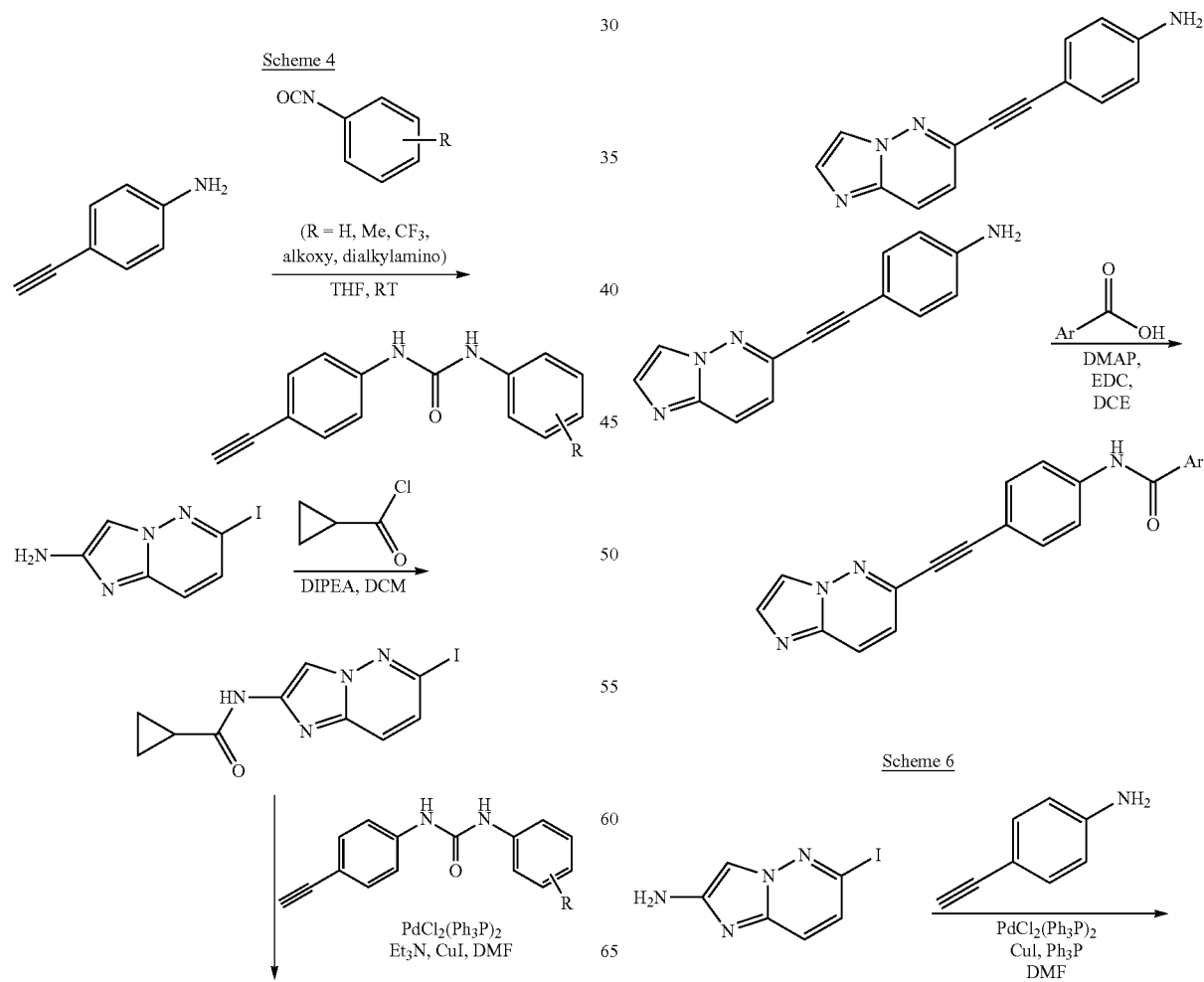
Scheme 4
Scheme 5
Scheme 6

31
-continued
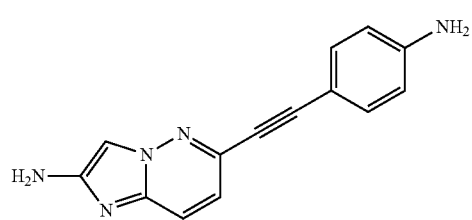
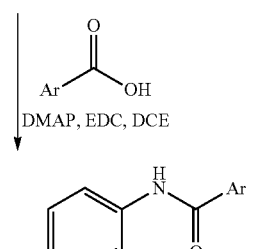
32
-continued
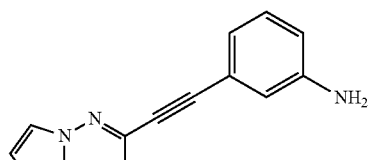
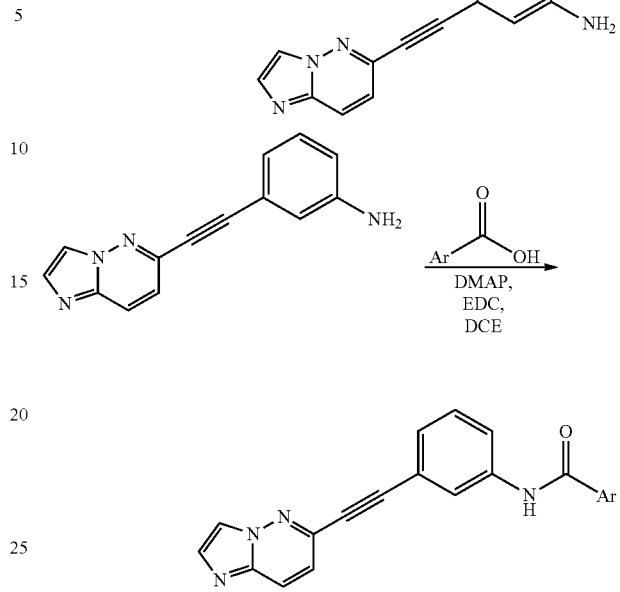
Scheme 7
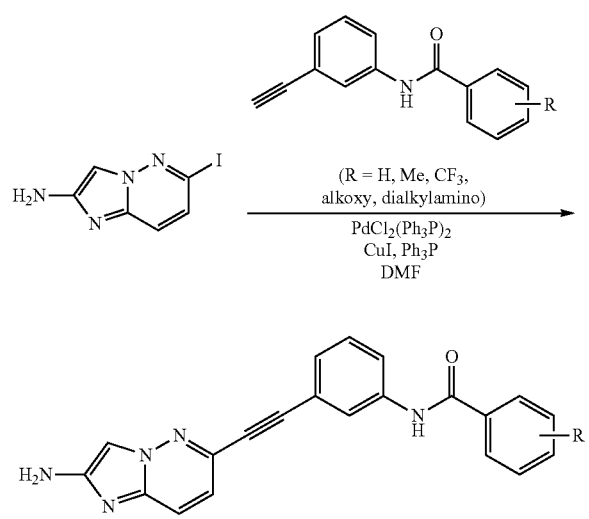
Scheme 8
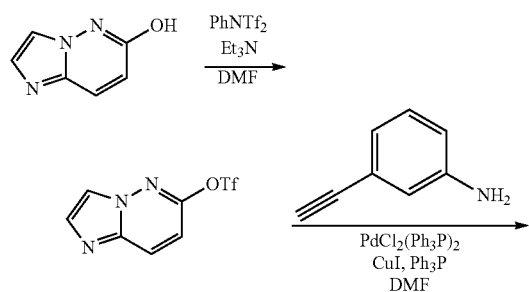
Scheme 9
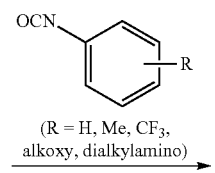
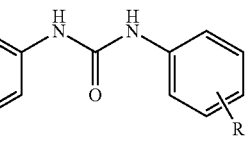
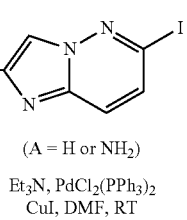
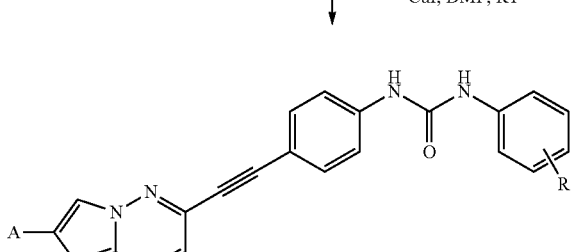

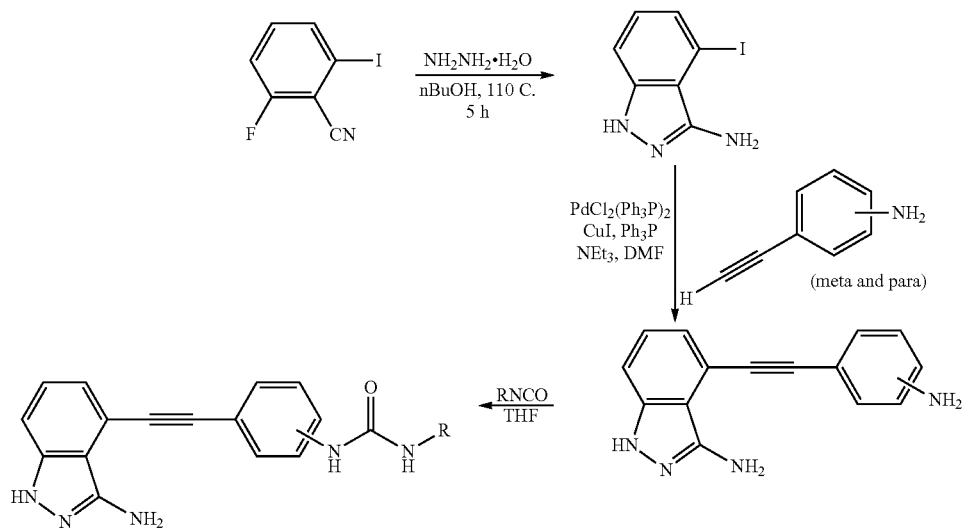

Those skilled in the art will appreciate that many additional compounds that fall under the scope of the invention can be prepared by performing various common chemical reactions. Details of certain specific chemical transformations are provided in the examples.

Those skilled in the art will be able to routinely modify and/or adapt the preceding schemes to synthesize any compounds described herein.

The present invention is not to be limited in scope by the exemplified embodiments which are intended as illustrations of single aspects of the invention only. Indeed, various modifications of the invention in addition to those described herein will become apparent to those skilled in the art from the foregoing description.

EXAMPLES

The following examples are for illustrative purposes only and are not intended, nor should they be construed as limiting the invention in any manner. Those skilled in the art will appreciate that variations and modifications of the following examples can be made without exceeding the spirit or scope of the invention.

Synthetic Examples

In general, characterization of the compounds was performed according to the following methods; NMR spectra are recorded on 300 or 600 MHz Varian and acquired at room temperature. Chemical shifts are given in ppm referenced either to internal TMS or to the solvent signal.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

In the Examples below, compounds were purified by medium pressure liquid chromatography, unless noted otherwise.

Example 1

1-{4-[(2-aminoimidazo[1,2-b]pyridazin-6-yl)ethynyl]phenyl}-3-(3-methylphenyl)urea

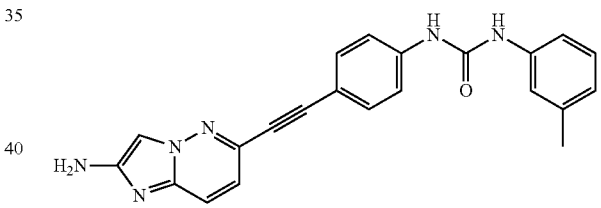

To a solution of 4-ethynylaniline (1.308 g, 11.18 mmol, 1 eq) in anhydrous THF (20 mL) under nitrogen atmosphere at room temperature was added dropwise m-tolyl isocyanate (1.684 mL, 1.2 eq). The yellow reaction solution was stirred at room temperature for 3 hours. The reaction was then partitioned between EtOAc and aq $NH_4Cl$. The organic layer was isolated, washed with saturated aq $NaHCO_3$, brine, and dried with anhydrous sodium sulfate. The upper solvent layer was decanted and concentrated. The resulting solid residue was chromatographed initially with EtOAc-Hex from 1:100 to 1:4 and then continued with an eluent from dichloromethane to MeOH-DCM 1:10. The product fractions were collected, concentrated, and the white solid was triturated with EtOAc-Hex (2:1) at room temperature for 18 h. Upon filtration, 1-(4-ethynylphenyl)-3-(3-methylphenyl)urea was obtained as white solid in amount of 2.134 g.

1-(4-ethynylphenyl)-3-(3-methylphenyl)urea $^1$H NMR (DMSO-$d_6$) δ: 8.85 (s, 1H), 8.63 (s, 1H), 7.45-7.48 (m, 2H), 7.37-7.40 (m, 2H), 7.29 (s, 1H), 7.21-7.23 (m, 1H), 7.16 (t, J=7.8 Hz, 1H), 6.80 (d, J=7.3 Hz, 1H), 4.03 (s, 1H), 2.27 (s, 3H).

To a nitrogen bubbled solution of 6-iodo-imidazo[1,2-b]pyridazin-2-ylamine (260 mg, 1 mmol, 1 eq) and 1-(4-ethynylphenyl)-3-(3-methylphenyl)urea (375 mg, 1.5 eq) in DMF (5 mL) was added triethylamine (0.56 mL, 4 eq), bis(triphenylphosphine)palladium(II) dichloride (70.2 mg, 0.1 eq), and copper(I) iodide (38.1 mg, 0.2 eq). The reaction mixture was stirred at room temperature for 10 minutes and then partitioned between saturated aq NaHCO$_3$ and i-PrOH—CHCl$_3$ (1:4). The aqueous layer was extracted once more with i-PrOH—CHCl$_3$ (1:4). The two organic layers were combined, washed with brine, and dried with anhydrous Na$_2$SO$_4$. The upper clear liquid was decanted, concentrated with silica gel, and the solid mixture was chromatographed (eluted from DCM to MeOH-DCM 1:15). The product fractions were collected and concentrated. The solid residue was triturated with EtOAc-Hex (1:1) and gave 1-{4-[(2-aminoimidazo[1,2-b]pyridazin-6-yl)ethynyl]phenyl}-3-(3-methylphenyl)urea as a brown solid upon filtration in amount of 133 mg.

1-{4-[(2-aminoimidazo[1,2-b]pyridazin-6-yl)ethynyl]phenyl}-3-(3-methylphenyl)urea

Example 1

$^1$H NMR (DMSO-d$_6$) δ: 8.94 (s, 1H), 8.68 (s, 1H), 7.64 (d, J=9.1 Hz, 1H), 7.52-7.56 (m, 4H), 7.35 (s, 1H), 7.30 (s, 1H), 7.24 (d, J=8.2 Hz, 1H), 7.17 (t, J=7.6 Hz, 1H), 7.14 (d, J=9.1 Hz, 1H), 6.81 (d, J=7.3 Hz, 1H), 5.68 (s, 2H), 2.28 (s, 3H).

Example 2

1-[4-(imidazo[1,2-b]pyridazin-6-ylethynyl)phenyl]-3-[3-(trifluoromethyl)phenyl]urea

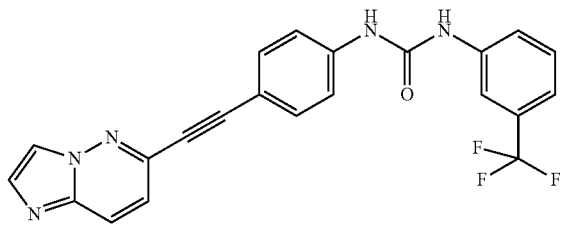 [SMILES: O=C(Nc1ccc(C#Cc2ccc3nccn3n2)cc1)Nc1cccc(C(F)(F)F)c1]

The compound of Example 2 was made in a manner analogous to Example 1 (see also Schemes 1, 2, and 9).

1-[4-(imidazo[1,2-b]pyridazin-6-ylethynyl)phenyl]-3-[3-(trifluoromethyl)phenyl]urea

Example 2

$^1$H NMR (DMSO-d$_6$) δ: 9.17 (s, 1H), 9.15 (s, 1H), 8.33 (s, 1H), 8.17 (d, J=9.7 Hz, 1H), 8.02 (s, 1H), 7.86 (d, J=1.2 Hz, 1H), 7.58-7.62 (m, 5H), 7.53 (t, J=7.9 Hz, 1H), 7.40 (d, J=9.1 Hz, 1H), 7.34 (d, J=7.6 Hz, 1H).

Example 3

1-[4-(imidazo[1,2-b]pyridazin-6-ylethynyl)phenyl]-3-(3-methylphenyl)urea

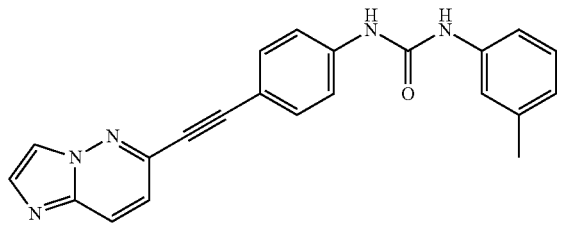

To a stirring mixture of 6-hydroxyimidazo[1,2-b]pyridazine (3.24 g, 24 mmol, 1 eq) in anhydrous DMF (25 mL) under nitrogen atmosphere was added triethylamine (13.4 mL, 4 eq) and N-phenyl-bis(trifluoromethanesulfonimide) (8.47 g, 1 eq). After 18 hours at room temperature, to the reaction was added triphenylphosphine (157 mg, 0.025 eq), bis(triphenylphosphine)palladium(II) dichloride (1.0 g, 0.06 eq), copper(I) iodide (914 mg, 0.2 eq), and a solution of 4-ethynylaniline (4.342 g, 1.5 eq) in DMF (10 mL) under nitrogen atmosphere. The resulting reaction mixture was heated at 60° C. for four hours. The reaction was then cooled to room temperature, diluted with ethyl acetate, washed sequentially with aqueous ammonium chloride, saturated aqueous sodium bicarbonate, brine, and lastly dried with anhydrous sodium sulfate. The upper solution was decanted, concentrated, the residue mixture was subject to a gradient column chromatography (EtOAc-Hex 1:3 to 3:1). The product fractions were collected, concentrated, and the residue was triturated with EtOAc-Hex (1:5) to give the first batch of as a yellow solid in amount of 1.277 g. The brown solid found as a remainder on top of the syringe column was re-subject to another gradient column chromatography (MeOH-DCM 1:200 to 1:30) to give a second batch of 4-(imidazo[1,2-b]pyridazin-6-ylethynyl)aniline in amount of 829 mg. The total yield was 2.106 g (37%).

4-(imidazo[1,2-b]pyridazin-6-ylethynyl)aniline $^1$H NMR (DMSO-d$_6$) δ: 8.28 (s, 1H), 8.11 (d, J=9.4 Hz, 1H), 7.82 (s, 1H), 7.30-7.33 (m, 3H), 6.58-6.61 (m, 2H), 5.81 (s, 2H).

A reaction mixture of 4-(imidazo[1,2-b]pyridazin-6-ylethynyl)aniline (93.6 mg, 0.4 mmol, 1 eq) and m-tolyl isocyanate (0.051 mL, 1 eq) in anhydrous THF (4 mL) was stirred at room temperature for four hours. It was then diluted with water and a solid which precipitated was filtered. The solid was further triturated with ethyl acetate and 1-[4-(imidazo[1,2-b]pyridazin-6-ylethynyl)phenyl]-3-(3-methylphenyl)urea was obtained as a yellow solid upon filtration in amount of 125 mg.

1-[4-(imidazo[1,2-b]pyridazin-6-ylethynyl)phenyl]-3-(3-methylphenyl)urea

Example 3

$^1$H NMR (DMSO-d$_6$) δ: 8.99 (s, 1H), 8.70 (s, 1H), 8.33 (s, 1H), 8.17 (d, J=9.4 Hz, 1H), 7.87 (br. s., 1H), 7.56-7.61 (m,

4H), 7.40 (d, J=9.4 Hz, 1H), 7.30 (s, 1H), 7.24 (d, J=8.5 Hz, 1H), 7.17 (t, J=7.8 Hz, 1H), 6.81 (d, J=7.6 Hz, 1H), 2.28 (s, 3H).

Example 4

1-{4-[(2-aminoimidazo[1,2-b]pyridazin-6-yl)ethynyl]phenyl}-3-[2-fluoro-5-(trifluoromethyl)phenyl]urea

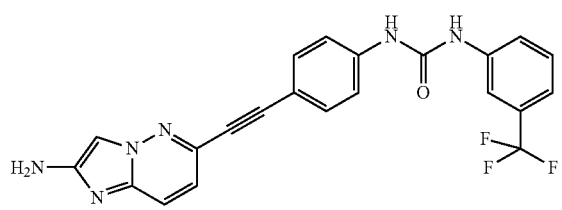 [SMILES: Nc1cn2nc(C#Cc3ccc(NC(=O)Nc4cccc(C(F)(F)F)c4)cc3)ccc2n1]

The compound of Example 4 was made by preparing 6-[(4-aminophenyl)ethynyl]imidazo[1,2-b]pyridazin-2-amine as in Example 20, followed by a procedure similar to Example 3 using 1-fluoro-2-isocyanato-4-(trifluoromethyl)benzene as the isocyanate (see also Schemes 1, 2, and 9).

1-{4-[(2-aminoimidazo[1,2-b]pyridazin-6-yl)ethynyl]phenyl}-3-[2-fluoro-5-(trifluoromethyl)phenyl]urea Example 4

$^1$H NMR (DMSO-$d_6$) δ: 9.46 (s, 1H), 9.00 (br. s., 1H), 8.60 (dd, J=7.2, 2.2 Hz, 1H), 7.65 (d, J=9.1 Hz, 1H), 7.57 (s, 3H), 7.49-7.55 (m, 2H), 7.40-7.43 (m, 1H), 7.35 (s, 1H), 7.15 (d, J=8.8 Hz, 1H), 5.69 (s, 2H).

Example 5

1-(3-chloro-4-fluorophenyl)-3-[4-(imidazo[1,2-b]pyridazin-6-ylethynyl)phenyl]urea

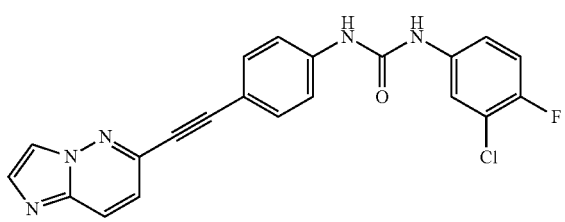 [SMILES: O=C(Nc1ccc(C#Cc2ccc3nccn3n2)cc1)Nc1ccc(F)c(Cl)c1]

The compound of Example 5 was made in a manner analogous to Example 1 (see also Schemes 1, 2, and 9).

1-(3-chloro-4-fluorophenyl)-3-[4-(imidazo[1,2-b]pyridazin-6-ylethynyl)phenyl]urea Example 5

$^1$H NMR (DMSO-$d_6$) δ: 9.11 (s, 1H), 8.99 (s, 1H), 8.33 (s, 1H), 8.17 (d, J=9.4 Hz, 1H), 7.87 (s, 1H), 7.80 (dd, J=6.7, 2.3 Hz, 1H), 7.57-7.62 (m, 4H), 7.40 (d, J=9.4 Hz, 1H), 7.33-7.37 (m, 2H).

Example 6

1-(2-fluoro-5-methylphenyl)-3-[4-(imidazo[1,2-b]pyridazin-6-ylethynyl)phenyl]urea

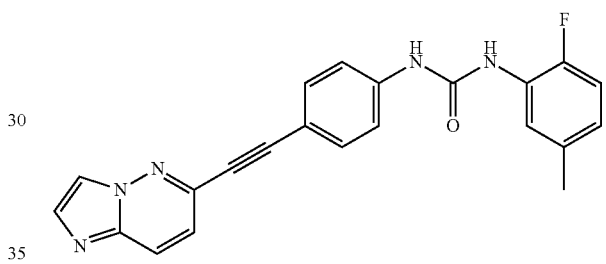

The compound of Example 6 was made in a manner analogous to Example 1 (see also Schemes 1, 2, and 9).

$^1$H NMR (DMSO-$d_6$) δ: 9.37 (s, 1H), 8.59 (d, J=2.3 Hz, 1H), 8.32 (s, 1H), 8.17 (d, J=9.7 Hz, 1H), 7.97 (dd, J=7.9, 1.8 Hz, 1H), 7.86 (d, J=1.2 Hz, 1H), 7.55-7.63 (m, 4H), 7.39 (d, J=9.4 Hz, 1H), 7.11 (dd, J=11.3, 8.4 Hz, 1H), 6.79-6.86 (m, 1H), 2.28 (s, 3H).

Example 7

1-[4-chloro-3-(trifluoromethyl)phenyl]-3-[4-(imidazo[1,2-b]pyridazin-6-ylethynyl)phenyl]urea

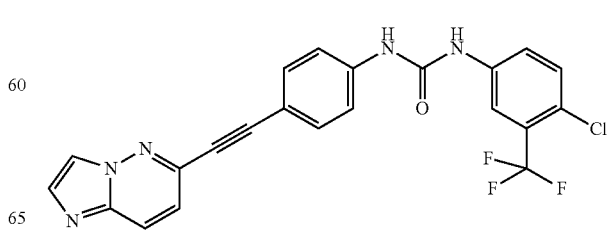

39

The compound of Example 7 was made in a manner analogous to Example 1 (see also Schemes 1, 2, and 9).

1-[4-chloro-3-(trifluoromethyl)phenyl]-3-[4-(imidazo[1,2-b]pyridazin-6-ylethynyl)phenyl]urea Example 7

¹H NMR (DMSO-d₆) δ: 9.29 (s, 1H), 9.20 (s, 1H), 8.33 (s, 1H), 8.17 (d, J=9.4 Hz, 1H), 8.12 (d, J=2.3 Hz, 1H), 7.86 (d, J=0.9 Hz, 1H), 7.65-7.67 (m, 1H), 7.64 (s, 1H), 7.58-7.63 (m, 4H), 7.40 (d, J=9.1 Hz, 1H).

Example 8

1-[4-(imidazo[1,2-b]pyridazin-6-ylethynyl)phenyl]-3-phenylurea

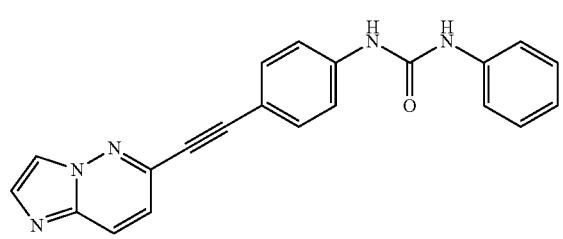 [SMILES: O=C(Nc1ccccc1)Nc1ccc(C#Cc2ccc3nccn3n2)cc1]

The compound of Example 8 was made in a manner analogous to Example 1 (see also Schemes 1, 2, and 9).

1-[4-(imidazo[1,2-b]pyridazin-6-ylethynyl)phenyl]-3-phenylurea

Example 8

¹H NMR (DMSO-d₆) δ: 9.02 (s, 1H), 8.79 (s, 1H), 8.33 (s, 1H), 8.17 (d, J=9.4 Hz, 1H), 7.86 (s, 1H), 7.57-7.61 (m, 4H), 7.47 (d, J=7.6 Hz, 2H), 7.40 (d, J=9.4 Hz, 1H), 7.30 (t, J=7.9 Hz, 2H), 6.99 (t, J=7.3 Hz, 1H).

40

Example 9

1-[2-fluoro-5-(trifluoromethyl)phenyl]-3-[4-(imidazo[1,2-b]pyridazin-6-ylethynyl)phenyl]urea

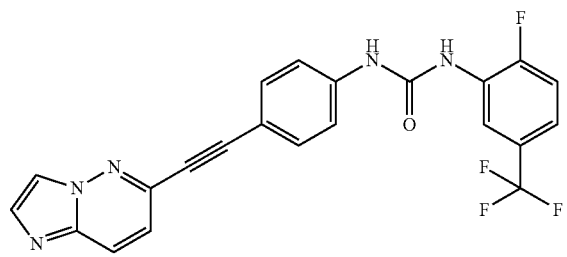 [SMILES: O=C(Nc1ccc(C#Cc2ccc3nccn3n2)cc1)Nc1cc(C(F)(F)F)ccc1F]

The compound of Example 9 was made in a manner analogous to Example 1 (see also Schemes 1, 2, and 9).

1-[2-fluoro-5-(trifluoromethyl)phenyl]-3-[4-(imidazo[1,2-b]pyridazin-6-ylethynyl)phenyl]urea Example 9

¹H NMR (DMSO-d₆) δ: 9.48 (s, 1H), 9.00 (br. s., 1H), 8.61 (dd, J=7.0, 2.1 Hz, 1H), 8.33 (s, 1H), 8.18 (d, J=9.4 Hz, 1H), 7.87 (d, J=0.9 Hz, 1H), 7.58-7.64 (m, 4H), 7.52 (dd, J=10.6, 8.8 Hz, 1H), 7.39-7.44 (m, 2H).

Example 10

1-[2-fluoro-5-(trifluoromethyl)phenyl]-3-[4-({2-[({[2-fluoro-5-(trifluoromethyl)phenyl]amino}carbonyl)amino]imidazo[1,2-b]pyridazin-6-yl}ethynyl)phenyl]urea

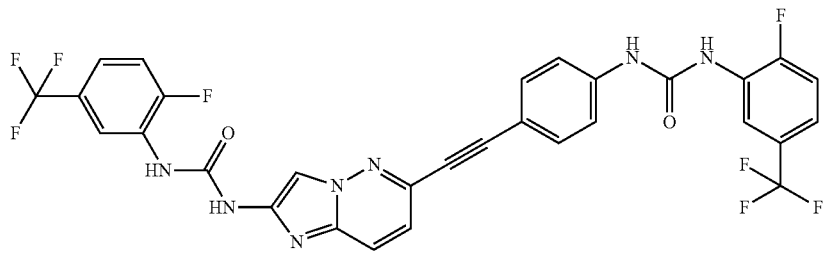 [SMILES: O=C(Nc1ccc(C#Cc2ccc3nc(NC(=O)Nc4cc(C(F)(F)F)ccc4F)cn3n2)cc1)Nc1cc(C(F)(F)F)ccc1F]

The compound of Example 10 was made by preparing 6-[(4-aminophenyl)ethynyl]imidazo[1,2-b]pyridazin-2-amine as in Example 20, followed by a procedure similar to Example 3 using 1-fluoro-2-isocyanato-4-(trifluoromethyl)benzene as the isocyanate (see also Schemes 1, 2, and 9).

1-[2-fluoro-5-(trifluoromethyl)phenyl]-3-[4-({2-[({[2-fluoro-5-(trifluoromethyl)phenyl]amino}carbonyl)amino]imidazo[1,2-b]pyridazin-6-yl}ethynyl)phenyl]urea Example 10

¹H NMR (DMSO-d₆) δ: 9.90 (br. s., 1H), 9.52 (br. s., 1H), 9.31 (br. s., 1H), 9.04 (br. s., 1H), 8.67 (dd, J=7.0, 1.8 Hz, 1H), 8.60 (dd, J=7.2, 1.9 Hz, 1H), 8.19 (s, 1H), 8.02 (d, J=9.1 Hz, 1H), 7.58-7.64 (m, 4H), 7.49-7.55 (m, 2H), 7.39-7.45 (m, 3H).

Example 11

N-(6-{[4-({[(3-methylphenyl)amino]carbonyl}amino)phenyl]ethynyl}imidazo[1,2-b]pyridazin-2-yl)acetamide

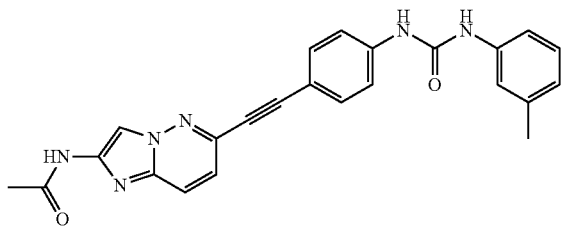 [SMILES: CC(=O)Nc1cn2nc(C#Cc3ccc(NC(=O)Nc4cccc(C)c4)cc3)ccc2n1]

A solution of 4-ethynylaniline (1.308 g, 11.18 mmol, 1 eq) and m-tolyl isocyanate (1.684 mL, 1.2 eq) in anhydrous THF (20 mL) was stirred under nitrogen atmosphere at room temperature for three hours. The yellow solution was diluted with ethyl acetate, washed sequentially with aqueous ammonium chloride, saturated aqueous sodium bicarbonate, brine, and lastly dried with anhydrous sodium sulfate. The clear solution was decanted, concentrated under reduced pressure to a lesser amount, and an off-white solid was obtained upon filtration. This solid was subject to a gradient column chromatography (EtOAc-Hex 1:100 to 1:4) followed by another column chromatography (from DCM to MeOH-DCM 1:10). 1-(4-ethynylphenyl)-3-(3-methylphenyl)urea was obtained as an off-white powder in amount of 2.134 g.

1-(4-ethynylphenyl)-3-(3-methylphenyl)urea $^1$H NMR (DMSO-$d_6$) δ: 8.85 (s, 1H), 8.63 (s, 1H), 7.45-7.48 (m, 2H), 7.37-7.39 (m, 2H), 7.29 (s, 1H), 7.21-7.24 (m, 1H), 7.16 (t, J=7.8 Hz, 1H), 6.80 (d, J=7.3 Hz, 1H), 4.03 (s, 1H), 2.27 (s, 3H).

To a 50-mL round bottom flask was added 6-iodo-imidazo[1,2-b]pyridazin-2-ylamine (130 mg, 0.5 mmol, 1 eq), anhydrous dichloromethane (10 mL), acetic anhydride (0.071 mL, 1.5 eq), pyridine (0.073 mL, 1.8 eq), and 4-(dimethylamino)pyridine (0.61 mg, 0.01 eq). After the mixture was stirred at room temperature for four hours, it was quenched with saturated aqueous sodium bicarbonate and extracted with i-PrOH—CHCl$_3$ (1:4). The organic layer was isolated, washed with brine, and dried with anhydrous sodium sulfate. The upper clear solution was decanted, concentrated, and the residue was subject to a gradient column chromatography (from DCM to MeOH-DCM 1:30) to yield N-(6-iodoimidazo[1,2-b]pyridazin-2-yl)acetamide as a white solid in amount of 67 mg.

N-(6-iodoimidazo[1,2-b]pyridazin-2-yl)acetamide $^1$H NMR (DMSO-$d_6$) δ: 10.90 (s, 1H), 8.25 (s, 1H), 7.73 (d, J=9.1 Hz, 1H), 7.49 (d, J=9.1 Hz, 1H), 1.99 (s, 3H).

To a solution of N-(6-iodoimidazo[1,2-b]pyridazin-2-yl)acetamide (65 mg, 0.215 mmol, 1 eq) and 1-(4-ethynylphenyl)-3-(3-methylphenyl)urea (80.7 mg, 1.5 eq) in anhydrous DMF (2 mL) under nitrogen atmosphere was added triethylamine (0.12 mL, 4 eq), bis(triphenylphosphine)palladium (II) dichloride (15 mg, 0.1 eq) and copper(I) iodide (8.2 mg, 0.2 eq). After the reaction mixture was stirred at room temperature for 10 minutes, it was diluted with ethyl acetate, washed sequentially with aqueous ammonium chloride, saturated aqueous sodium bicarbonate, brine, and lastly dried with anhydrous sodium sulfate. The upper solution was decanted, concentrated, and the oily residue was wrapped with silica gel which was subject to a gradient column chromatography (from DCM to MeOH-DCM 1:9) to give N-(6-{[4-({[(3-methylphenyl)amino]carbonyl}amino)phenyl]ethynyl}imidazo[1,2-b]pyridazin-2-yl)acetamide as a brown solid in amount of 31 mg.

N-(6-{[4-({[(3-methylphenyl)amino]carbonyl}amino)phenyl]ethynyl}imidazo[1,2-b]pyridazin-2-yl)acetamide Example 11

$^1$H NMR (DMSO-$d_6$) δ: 10.95 (s, 1H), 8.99 (s, 1H), 8.70 (s, 1H), 8.26 (s, 1H), 8.01 (d, J=9.4 Hz, 1H), 7.57 (s, 4H), 7.38 (d, J=9.4 Hz, 1H), 7.30 (s, 1H), 7.22-7.27 (m, 1H), 7.14-7.20 (m, 1H), 6.81 (d, J=7.3 Hz, 1H), 2.29 (s, 3H), 2.11 (s, 3H).

Example 12

N-(6-{[4-({[(3-methylphenyl)amino]carbonyl}amino)phenyl]ethynyl}imidazo[1,2-b]pyridazin-2-yl)cyclopropanecarboxamide

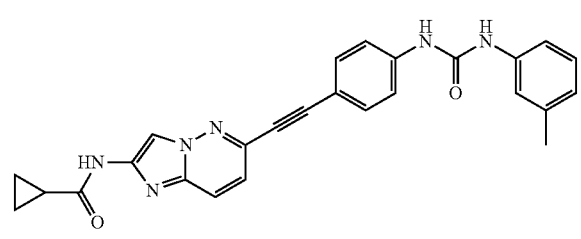 [SMILES: Cc1cccc(NC(=O)Nc2ccc(C#Cc3ccc4nc(NC(=O)C5CC5)cn4n3)cc2)c1]

To the mixture of 6-iodo-imidazo[1,2-b]pyridazin-2-ylamine (130 mg, 0.5 mmol, 1 eq) and N,N-diisopropylethylamine (0.26 mL, 3 eq) in anhydrous dichloromethane (10 mL) at room temperature was added dropwise cyclopropane carbonyl chloride (0.26 mL, 3 eq). After the reaction mixture was stirred at ambient temperature for two hours, it was partitioned between saturated aqueous sodium bicarbonate and ethyl acetate (with 10% THF added). The organic layer was isolated, washed with brine, and dried with anhydrous sodium sulfate. The upper clear solution was decanted, concentrated, and the residue was subject to a gradient column chromatography (from DCM to MeOH-DCM 1:30) to give N-(6-iodoimidazo[1,2-b]pyridazin-2-yl)cyclopropanecarboxamide as a white powder in amount of 51 mg.

N-(6-iodoimidazo[1,2-b]pyridazin-2-yl)cyclopropanecarboxamide

¹H NMR (DMSO-d₆) δ: 11.19 (s, 1H), 8.23 (s, 1H), 7.74 (d, J=9.1 Hz, 1H), 7.49 (d, J=9.4 Hz, 1H), 1.92-1.97 (m, 1H), 0.81-0.85 (m, 4H).

To a mixture of N-(6-iodoimidazo[1,2-b]pyridazin-2-yl)cyclopropanecarboxamide (50 mg, 0.152 mmol, 1 eq) and 1-(4-ethynylphenyl)-3-(3-methylphenyl)urea (57 mg, 1.5 eq) in anhydrous DMF (1 mL) under nitrogen atmosphere was added triethylamine (0.085 mL, 4 eq), bis(triphenylphosphine)palladium(II) dichloride (10.7 mg, 0.1 eq) and copper (I) iodide (5.8 mg, 0.2 eq). After the reaction mixture was stirred at room temperature for 10 minutes, it was diluted with ethyl acetate, washed sequentially with aqueous ammonium chloride, saturated aqueous sodium bicarbonate, brine, and lastly dried with anhydrous sodium sulfate. The upper solution was decanted, concentrated, and the solid residue was subject to a gradient column chromatography (from DCM to MeOH-DCM 1:9). The products' fractions were collected, concentrated, and the solid residue was triturated with EtOAc-Hex (6:1) to give N-(6-{[4-({[(3-methylphenyl)amino]carbonyl}amino)phenyl]ethynyl}imidazo[1,2-b]pyridazin-2-yl)cyclopropanecarboxamide as a brown solid upon filtration in amount of 46 mg.

N-(6-{[4-({[(3-methylphenyl)amino]carbonyl}amino)phenyl]ethynyl}imidazo[1,2-b]pyridazin-2-yl)cyclopropanecarboxamide Example 12

¹H NMR (DMSO-d₆) δ: 11.24 (s, 1H), 8.97 (s, 1H), 8.69 (s, 1H), 8.25 (s, 1H), 8.01 (d, J=9.4 Hz, 1H), 7.57 (s, 4H), 7.38 (d, J=9.1 Hz, 1H), 7.30 (s, 1H), 7.21-7.27 (m, 1H), 7.13-7.21 (m, 1H), 6.81 (d, J=7.3 Hz, 1H), 2.28 (s, 3H), 1.91-2.02 (m, 1H), 0.80-0.91 (m, 4H).

Example 13

1-[4-(imidazo[1,2-b]pyridazin-6-ylethynyl)phenyl]-3-(4-methylphenyl)urea

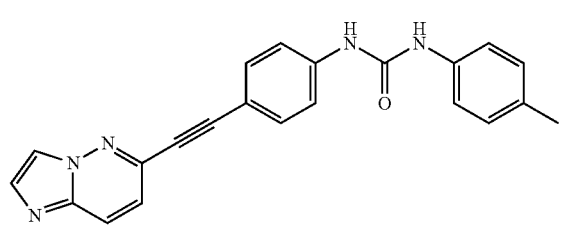 [SMILES: Cc1ccc(NC(=O)Nc2ccc(C#Cc3ccc4nccn4n3)cc2)cc1]

The compound of Example 14 was made in a manner analogous to Example 1 (see also Schemes 1, 2, and 9).

1-[4-(imidazo[1,2-b]pyridazin-6-ylethynyl)phenyl]-3-(4-methylphenyl)urea

Example 13

¹H NMR (DMSO-d₆) δ: 8.96 (s, 1H), 8.67 (s, 1H), 8.33 (s, 1H), 8.17 (d, J=9.4 Hz, 1H), 7.87 (br. s., 1H), 7.55-7.60 (m, 4H), 7.40 (d, J=9.4 Hz, 1H), 7.35 (d, J=8.5 Hz, 2H), 7.10 (d, J=8.2 Hz, 2H), 2.25 (s, 3H).

Example 14

1-{6-[(4-aminophenyl)ethynyl]imidazo[1,2-b]pyridazin-2-yl}-3-(3-chloro-4-fluorophenyl)urea

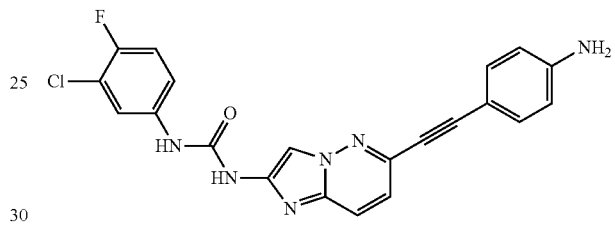

The compound of Example 14 was made by preparing 6-[(4-aminophenyl)ethynyl]imidazo[1,2-b]pyridazin-2-amine as in Example 20, followed by a procedure similar to Example 3 using 2-chloro-1-fluoro-4-isocyanatobenzene as the isocyanate (see also Schemes 1, 2, and 9).

1-{6-[(4-aminophenyl)ethynyl]imidazo[1,2-b]pyridazin-2-yl}-3-(3-chloro-4-fluorophenyl)urea Example 14

¹H NMR (DMSO-d₆) δ: 9.49 (s, 1H), 9.18 (br. s., 1H), 8.09 (s, 1H), 7.93-7.96 (m, 2H), 7.86 (dd, J=6.7, 2.3 Hz, 1H), 7.33-7.38 (m, 2H), 7.28-7.32 (m, 2H), 6.57-6.61 (m, 2H), 5.78 (s, 2H).

Example 15

1-(3-chloro-4-fluorophenyl)-3-(4-{[2-({[(3-chloro-4-fluorophenyl)amino]carbonyl}amino)imidazo[1,2-b]pyridazin-6-yl]ethynyl}phenyl)urea

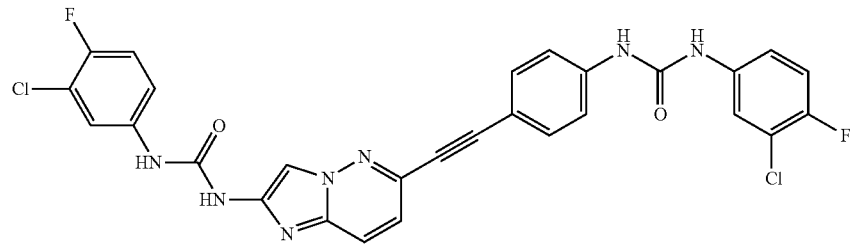 [SMILES: O=C(Nc1ccc(C#Cc2ccc3nc(NC(=O)Nc4ccc(F)c(Cl)c4)cn3n2)cc1)Nc1ccc(F)c(Cl)c1]

The compound of Example 15 was by preparing 6-[(4-aminophenyl)ethynyl]imidazo[1,2-b]pyridazin-2-amine as in Example 20, followed by a procedure similar to Example 3 using 2-chloro-1-fluoro-4-isocyanatobenzene as the isocyanate (see also Schemes 1, 2, and 9).

1-(3-chloro-4-fluorophenyl)-3-(4-{[2-({[(3-chloro-4-fluorophenyl)amino]carbonyl}amino)imidazo[1,2-b]pyridazin-6-yl]ethynyl}phenyl)urea Example 15

$^1$H NMR (DMSO-d$_6$) δ: 9.52 (s, 1H), 9.17 (s, 1H), 9.11 (s, 1H), 9.00 (s, 1H), 8.14 (s, 1H), 8.00 (d, J=9.4 Hz, 1H), 7.86 (dd, J=6.7, 2.3 Hz, 1H), 7.80 (dd, J=6.7, 2.3 Hz, 1H), 7.55-7.61 (m, 4H), 7.32-7.40 (m, 5H).

Example 16

2-fluoro-N-[4-(imidazo[1,2-b]pyridazin-6-ylethynyl)phenyl]-5-(trifluoromethyl)benzamide

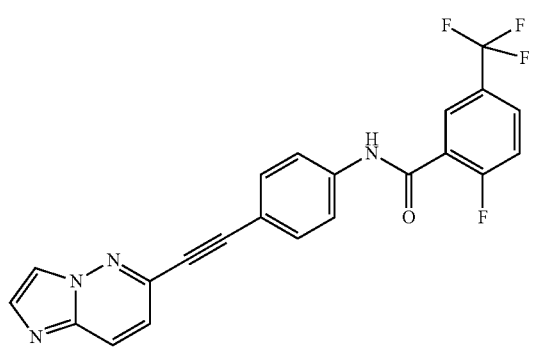 [SMILES: O=C(Nc1ccc(C#Cc2ccc3nccn3n2)cc1)c1cc(C(F)(F)F)ccc1F]

The compound of Example 16 was made in a manner analogous to Example 17 below (see also Schemes 5, 6, 7, and 8).

2-fluoro-N-[4-(imidazo[1,2-b]pyridazin-6-ylethynyl)phenyl]-5-(trifluoromethyl)benzamide Example 16

$^1$H NMR (DMSO-d$_6$) δ: 10.89 (s, 1H), 8.34 (s, 1H), 8.19 (dd, J=9.4, 0.6 Hz, 1H), 8.11 (dd, J=6.0, 1.9 Hz, 1H), 8.02 (ddd, J=8.4, 4.3, 2.5 Hz, 1H), 7.88 (d, J=1.2 Hz, 1H), 7.84 (d, J=8.5 Hz, 2H), 7.69-7.72 (m, 2H), 7.65 (t, J=9.0 Hz, 1H), 7.42 (d, J=9.4 Hz, 1H).

Example 17

2-fluoro-N-[4-(imidazo[1,2-b]pyridazin-6-ylethynyl)phenyl]-5-methylbenzamide

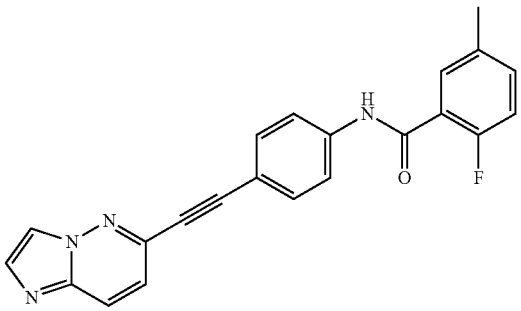 [SMILES: Cc1ccc(F)c(C(=O)Nc2ccc(C#Cc3ccc4nccn4n3)cc2)c1]

To the solution of 4-(imidazo[1,2-b]pyridazin-6-ylethynyl)aniline (93.6 mg, 0.4 mmol, 1 eq) and 2-fluoro-4-methylbenzoic acid (62.3 mg, 1 eq) in anhydrous dichloroethane (3 mL) under nitrogen atmosphere at room temperature was added 4-(dimethylamino)pyridine (10 mg, 0.2 eq) and N-(3-dimethylaminopropyl)-N'-ethylcarbodiimide hydrochloride (92.2 mg, 1.2 eq). After the reaction was stirred at 60° C. for 3 hours, it was diluted with ethyl acetate, washed sequentially with aqueous ammonium chloride, saturated aqueous sodium bicarbonate, brine, and lastly dried with anhydrous sodium sulfate. The upper solution was decanted, concentrated, and the solid residue was triturated with EtOAc-Hex (2:1) to yield 2-fluoro-N-[4-(imidazo[1,2-b]pyridazin-6-ylethynyl)phenyl]-5-methylbenzamide as a slightly yellow solid in amount of 122 mg.

2-fluoro-N-[4-(imidazo[1,2-b]pyridazin-6-ylethynyl)phenyl]-5-methylbenzamide

Example 17

$^1$H NMR (DMSO-d$_6$) δ: 10.66 (s, 1H), 8.34 (s, 1H), 8.19 (d, J=9.4 Hz, 1H), 7.87 (d, J=0.9 Hz, 1H), 7.85 (d, J=8.5 Hz, 2H), 7.66-7.69 (m, 2H), 7.49 (dd, J=6.7, 1.8 Hz, 1H), 7.42 (d, J=9.4 Hz, 1H), 7.39 (ddd, J=8.1, 5.3, 2.2 Hz, 1H), 7.25 (dd, J=9.8, 8.7 Hz, 1H), 2.35 (s, 3H).

Example 18

N-[4-(imidazo[1,2-b]pyridazin-6-ylethynyl)phenyl]-3-methyl-2-furamide

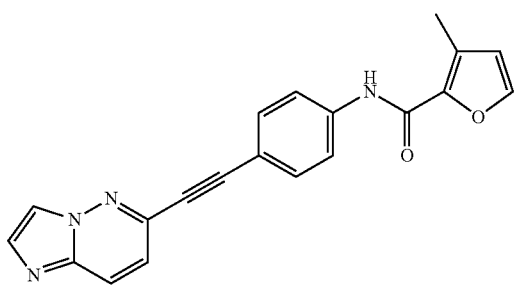 [SMILES: Cc1ccoc1C(=O)Nc1ccc(C#Cc2ccc3nccn3n2)cc1]

The compound of Example 18 was made in a manner analogous to Example 17 (see also Schemes 5, 6, 7, and 8).

N-[4-(imidazo[1,2-b]pyridazin-6-ylethynyl)phenyl]-3-methyl-2-furamide

Example 18

$^1$H NMR (DMSO-d$_6$) δ: 10.33 (s, 1H), 8.34 (s, 1H), 8.18 (d, J=9.1 Hz, 1H), 7.91-7.94 (m, 2H), 7.87 (d, J=1.2 Hz, 1H), 7.83 (d, J=1.5 Hz, 1H), 7.62-7.65 (m, 2H), 7.41 (d, J=9.4 Hz, 1H), 6.62 (d, J=1.5 Hz, 1H), 2.36 (s, 3H).

Example 19

N-{4-[(2-aminoimidazo[1,2-b]pyridazin-6-yl)ethynyl]phenyl}benzamide

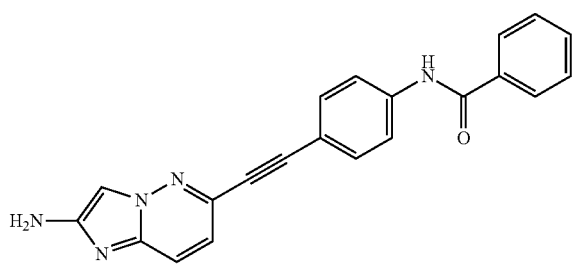 [SMILES: Nc1cn2nc(C#Cc3ccc(NC(=O)c4ccccc4)cc3)ccc2n1]

The compound of Example 19 was made in a manner analogous to Example 20 below (see also Schemes 5, 6, 7, and 8).

N-{4-[(2-aminoimidazo[1,2-b]pyridazin-6-yl)ethynyl]phenyl}benzamide

Example 19

$^1$H NMR (DMSO-d$_6$) δ: 10.48 (s, 1H), 7.95-7.98 (m, 2H), 7.89-7.92 (m, 2H), 7.66 (d, J=9.1 Hz, 1H), 7.60-7.63 (m, 3H), 7.54-7.57 (m, 2H), 7.36 (s, 1H), 7.16 (d, J=8.8 Hz, 1H), 5.70 (s, 2H).

Example 20

N-{4-[(2-aminoimidazo[1,2-b]pyridazin-6-yl)ethynyl]phenyl}-2-fluoro-5-methylbenzamide

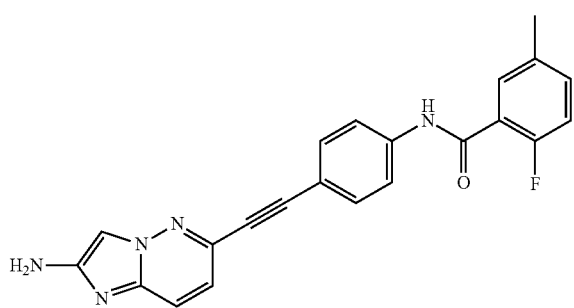 [SMILES: Cc1ccc(F)c(C(=O)Nc2ccc(C#Cc3ccc4nc(N)cn4n3)cc2)c1]

To the mixture of 6-iodo-imidazo[1,2-b]pyridazin-2-ylamine (780 mg, 3.0 mmol, 1 eq) and 4-ethynylaniline (543 mg, 1.5 eq) in anhydrous DMF (10 mL) under nitrogen atmosphere was added triethylamine (1.67 mL, 4 eq), bis(triphenylphosphine)palladium(II) dichloride (210 mg, 0.1 eq) and copper(I) iodide (114 mg, 0.2 eq). After the reaction mixture was stirred at 50° C. for 30 minutes, it was partitioned between saturated aqueous sodium bicarbonate and chloroform (containing 3% v/v of MeOH). The organic layer was separated and washed with aqueous ammonium chloride, brine, and lastly dried with anhydrous sodium sulfate. The upper suspension mixture was decanted, concentrated, and the solid residue was subject to a gradient column chromatography (from CHCl$_3$ to MeOH—CHCl$_3$ 1:30) to give 6-[(4-aminophenyl)ethynyl]imidazo[1,2-b]pyridazin-2-amine as a yellow solid in amount of 166 mg.

6-[(4-aminophenyl)ethynyl]imidazo[1,2-b]pyridazin-2-amine $^1$H NMR (DMSO-d$_6$) δ: 7.62 (d, J=8.8 Hz, 1H), 7.33 (br. s., 1H), 7.24-7.27 (m, 2H), 7.07 (d, J=9.1 Hz, 1H), 6.56-6.59 (m, 2H), 5.71 (br. s., 2H), 5.64 (br. s., 2H).

To 6-[(4-aminophenyl)ethynyl]imidazo[1,2-b]pyridazin-2-amine, (30 mg, 0.12 mmol, 1 eq) and 2-fluoro-5-methylbenzoic acid (18.5 mg, 1 eq) in anhydrous dichloroethane (1 mL) under nitrogen atmosphere at room temperature was added 4-(dimethylamino)pyridine (2.94 mg, 0.2 eq) and N-(3-dimethylaminopropyl)-N'-ethylcarbodiimide hydrochloride (27.76 mg, 1.2 eq). After the reaction was stirred at 50° C. for 2 hours, it was diluted with chloroform, washed sequentially with aqueous ammonium chloride, saturated aqueous sodium bicarbonate, brine, and lastly dried with anhydrous sodium sulfate. The upper solution was decanted, concentrated, and the solid residue was subject to a gradient column chromatography (from CHCl$_3$ to MeOH—CHCl$_3$ 1:25) to yield N-{4-[(2-aminoimidazo[1,2-b]pyridazin-6-yl)ethynyl]phenyl}-2-fluoro-5-methylbenzamide as a yellow solid in amount of 7 mg.

N-{4-[(2-aminoimidazo[1,2-b]pyridazin-6-yl)ethynyl]phenyl}-2-fluoro-5-methylbenzamide Example 20

$^1$H NMR (DMSO-d$_6$) δ: 10.62 (s, 1H), 7.82 (d, J=8.5 Hz, 2H), 7.65 (d, J=9.1 Hz, 1H), 7.60-7.63 (m, 2H), 7.48 (dd, J=6.5, 1.8 Hz, 1H), 7.37-7.41 (m, 1H), 7.36 (s, 1H), 7.25 (dd, J=9.8, 8.7 Hz, 1H), 7.16 (d, J=8.8 Hz, 1H), 5.70 (s, 2H), 2.35 (s, 3H).

Example 21

N-{3-[(2-aminoimidazo[1,2-b]pyridazin-6-yl)ethynyl]phenyl}-2-fluoro-5-methylbenzamide

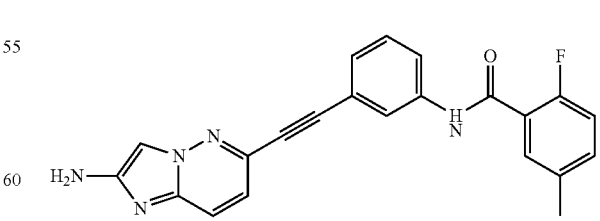

To the nitrogen bubbled solution of 6-iodo-imidazo[1,2-b]pyridazin-2-ylamine (52 mg, 0.2 mmol, 1 eq) in anhydrous DMF (2 mL) was added triethylamine (0.11 mL, 4 eq), bis (triphenylphosphine)palladium(II) dichloride (14 mg, 0.1 eq), copper(I) iodide (7.6 mg, 0.2 eq), and N-(3-ethynylphenyl)-2-fluoro-5-methylbenzamide (76 mg, 1.5 eq). after the mixture was stirred at room temperature for 30 minutes, it was diluted with ethyl acetate, washed sequentially with aqueous ammonium chloride, saturated aqueous sodium bicarbonate, brine, and lastly dried with anhydrous sodium sulfate. The upper solution was decanted, concentrated, and the solid residue was subject to a gradient column chromatography [EtOAc-Hex 1:2 to 3:1 (with 1% v/v MeOH added)]. The product fractions were collected, concentrated, the residue was further triturated with ethyl acetate to give N-{3-[(2-aminoimidazo[1,2-b]pyridazin-6-yl)ethynyl]phenyl}-2-fluoro-5-methylbenzamide as a yellow solid in amount of 23 mg.

N-{3-[(2-aminoimidazo[1,2-b]pyridazin-6-yl)ethynyl]phenyl}-2-fluoro-5-methylbenzamide Example 21

$^1$H NMR (DMSO-d$_6$) δ: 10.54 (s, 1H), 8.06 (s, 1H), 7.74 (d, J=7.9 Hz, 1H), 7.66 (d, J=9.1 Hz, 1H), 7.49 (dd, J=6.6, 1.9 Hz, 1H), 7.45 (t, J=7.9 Hz, 1H), 7.36-7.41 (m, 3H), 7.25 (dd, J=9.8, 8.7 Hz, 1H), 7.20 (d, J=8.8 Hz, 1H), 5.73 (s, 2H), 2.35 (s, 3H).

Example 22

N-[3-(imidazo[1,2-b]pyridazin-6-ylethynyl)phenyl]-3-(trifluoromethyl)benzamide

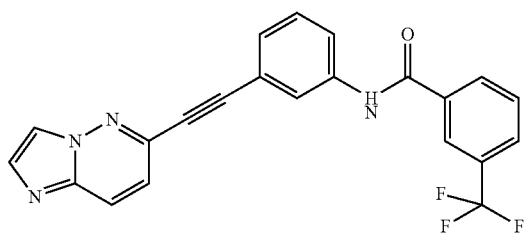 [SMILES: O=C(Nc1cccc(C#Cc2ccc3nccn3n2)c1)c1cccc(C(F)(F)F)c1]

The compound of Example 22 was made in a manner analogous to Example 17 (see also Schemes 5, 6, 7, and 8).

N-[3-(imidazo[1,2-b]pyridazin-6-ylethynyl)phenyl]-3-(trifluoromethyl)benzamide

Example 22

$^1$H NMR (DMSO-d$_6$) δ: 10.64 (s, 1H), 8.36 (5, 1H), 8.32 (s, 1H), 8.29 (d, J=8.5 Hz, 1H), 8.21 (d, J=9.4 Hz, 1H), 8.17 (t, J=1.6 Hz, 1H), 8.00 (d, J=8.2 Hz, 1H), 7.89 (d, J=1.2 Hz, 1H), 7.86-7.89 (m, 1H), 7.82 (t, J=7.9 Hz, 1H), 7.50-7.53 (m, 1H), 7.44-7.47 (m, 2H).

Example 23

N-[3-(imidazo[1,2-b]pyridazin-6-ylethynyl)phenyl]-3-methylbenzamide

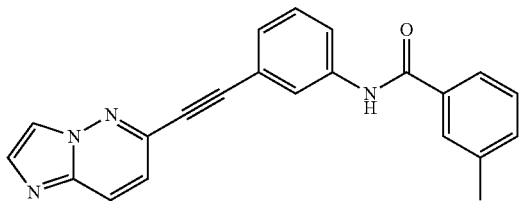 [SMILES: Cc1cccc(C(=O)Nc2cccc(C#Cc3ccc4nccn4n3)c2)c1]

To a stirring mixture of 6-hydroxyimidazo[1,2-b]pyridazine (2.06 g, 15.259 mmol, 1 eq) in anhydrous DMF (20 mL) under nitrogen atmosphere was added triethylamine (8.51 mL, 4 eq) and N-phenyl-bis(trifluoromethanesulfonimide) (5.386 g, 1 eq). After the reaction was stirred at room temperature for 18 hours, to the reaction was added triphenylphosphine (100 mg, 0.025 eq), bis(triphenylphosphine) palladium(II) dichloride (1.07 g, 0.1 eq), copper(I) iodide (581 mg, 0.2 eq), and 3-ethynylaniline (2.394 mL, 1.5 eq) under nitrogen atmosphere. The resulting reaction mixture was heated at 60° C. for two hours. The reaction was then cooled to room temperature, diluted with ethyl acetate, washed sequentially with aqueous ammonium chloride, saturated aqueous sodium bicarbonate, brine, and lastly dried with anhydrous sodium sulfate. The upper solution was decanted, concentrated, the residue mixture was subject to a gradient column chromatography (from DCM to MeOH-DCM 1:25). The product fractions were collected, concentrated, and the residue was triturated with EtOAc-Hex (~1:5) to give 3-(imidazo[1,2-b]pyridazin-6-ylethynyl)aniline as a fluffy slightly yellow solid upon filtration in amount of 2.384 g (67%).

3-(imidazo[1,2-b]pyridazin-6-ylethynyl)aniline $^1$H NMR (DMSO-d$_6$) δ: 8.33 (s, 1H), 8.17 (d, J=9.4 Hz, 1H), 7.87 (s, 1H), 7.39 (d, J=9.4 Hz, 1H), 7.11 (t, J=7.9 Hz, 1H), 6.81 (t, J=1.8 Hz, 1H), 6.78 (d, J=7.3 Hz, 1H), 6.69 (dd, J=8.2, 1.5 Hz, 1H), 5.36 (s, 2H).

To a mixture of 3-(imidazo[1,2-b]pyridazin-6-ylethynyl) aniline (93.6 mg, 0.4 mmol, 1 eq) and m-toluic acid (55 mg, 1 eq) in anhydrous dichloroethane (4 mL) under nitrogen atmosphere was added 4-(dimethylamino)pyridine (10 mg, 0.2 eq) and N-(3-dimethylaminopropyl)-N'-ethylcarbodiimide hydrochloride (92.2 mg, 1.2 eq). After the reaction was stirred at 60° C. for four hours and was cooled to room temperature, white precipitates were observed. It was filtered directly to give a white solid. This solid was further subject to a gradient column chromatography (MeOH-DCM 1:50 to 1:20) to yield N-[3-(imidazo[1,2-b]pyridazin-6-ylethynyl) phenyl]-3-methylbenzamide as a white solid in amount of 85 mg.

N-[3-(imidazo[1,2-b]pyridazin-6-ylethynyl)phenyl]-3-methylbenzamide

Example 23

$^1$H NMR (DMSO-d$_6$) δ: 10.39 (s, 1H), 8.36 (s, 1H), 8.20 (d, J=9.4 Hz, 1H), 8.18 (t, J=1.6 Hz, 1H), 7.89 (d, J=1.2 Hz, 1H), 7.86-7.88 (m, 1H), 7.79 (s, 1H), 7.76 (ddd, J=6.1, 2.2, 2.0 Hz, 1H), 7.40-7.50 (m, 5H), 2.41 (s, 3H).

Example 24

3-chloro-4-fluoro-N-[3-(imidazo[1,2-b]pyridazin-6-ylethynyl)phenyl]benzamide

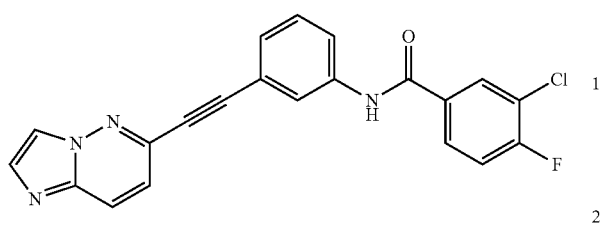

The compound of Example 24 was made in a manner analogous to Example 17 (see also Schemes 5, 6, 7, and 8).

3-chloro-4-fluoro-N-[3-(imidazo[1,2-b]pyridazin-6-ylethynyl)phenyl]benzamide

Example 24

$^1$H NMR (DMSO-d$_6$) δ: 10.51 (s, 1H), 8.36 (s, 1H), 8.23 (dd, J=7.0, 2.3 Hz, 1H), 8.21 (d, J=9.4 Hz, 1H), 8.15 (t, J=1.8 Hz, 1H), 8.02 (ddd, J=8.6, 4.8, 2.2 Hz, 1H), 7.89 (d, J=1.2 Hz, 1H), 7.83-7.86 (m, 1H), 7.63 (t, J=8.8 Hz, 1H), 7.49-7.52 (m, 1H), 7.43-7.47 (m, 2H).

Example 25

N-[3-(imidazo[1,2-b]pyridazin-6-ylethynyl)phenyl]-1-benzofuran-2-carboxamide

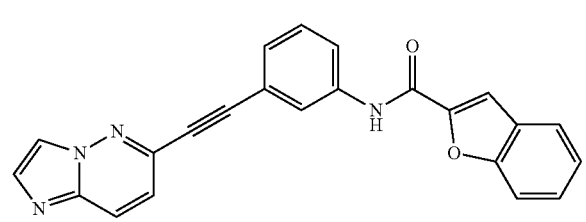 [SMILES: O=C(Nc1cccc(C#Cc2ccc3nccn3n2)c1)c1cc2ccccc2o1]

The compound of Example 25 was made in a manner analogous to Example 17 (see also Schemes 5, 6, 7, and 8).

N-[3-(imidazo[1,2-b]pyridazin-6-ylethynyl)phenyl]-1-benzofuran-2-carboxamide

Example 25

$^1$H NMR (DMSO-d$_6$) δ: 10.73 (s, 1H), 8.36 (s, 1H), 8.20-8.22 (m, 2H), 7.92 (dd, J=8.2, 1.2 Hz, 1H), 7.89 (d, J=0.9 Hz, 1H), 7.85 (d, J=7.6 Hz, 1H), 7.82 (s, 1H), 7.75 (d, J=8.2 Hz, 1H), 7.50-7.55 (m, 2H), 7.44-7.48 (m, 2H), 7.37-7.41 (m, 1H).

Example 26

2-fluoro-N-[3-(imidazo[1,2-b]pyridazin-6-ylethynyl)phenyl]-5-methylbenzamide

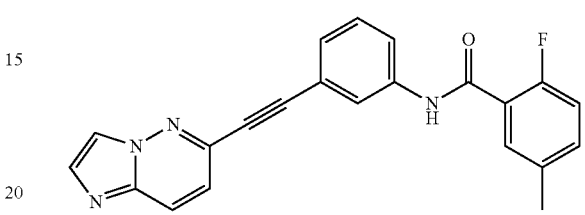

The compound of Example 26 was made in a manner analogous to Example 17 (see also Schemes 5, 6, 7, and 8).

2-fluoro-N-[3-(imidazo[1,2-b]pyridazin-6-ylethynyl)phenyl]-5-methylbenzamide

Example 26

$^1$H NMR (DMSO-d$_6$) δ: 10.57 (s, 1H), 8.36 (s, 1H), 8.20 (d, J=9.4 Hz, 1H), 8.12 (s, 1H), 7.89 (d, J=1.2 Hz, 1H), 7.77 (d, J=8.2 Hz, 1H), 7.45-7.51 (m, 3H), 7.42-7.44 (m, 1H), 7.38-7.41 (m, 1H), 7.25 (dd, J=9.8, 8.7 Hz, 1H), 2.36 (s, 3H).

Example 27

N-[3-(imidazo[1,2-b]pyridazin-6-ylethynyl)phenyl]benzamide

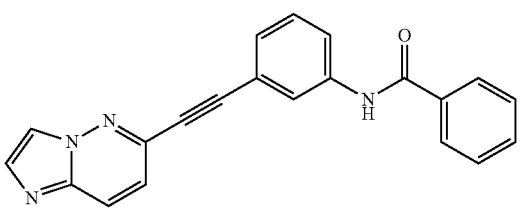 [SMILES: O=C(Nc1cccc(C#Cc2ccc3nccn3n2)c1)c1ccccc1]

The compound of Example 27 was made in a manner analogous to Example 17 (see also Schemes 5, 6, 7, and 8).

N-[3-(imidazo[1,2-b]pyridazin-6-ylethynyl)phenyl]benzamide

Example 27

$^1$H NMR (DMSO-d$_6$) δ: 10.43 (s, 1H), 8.36 (s, 1H), 8.20 (d, J=9.4 Hz, 1H), 8.19 (t, J=1.8 Hz, 1H), 7.96-7.99 (m, 2H), 7.89

(d, J=1.2 Hz, 1H), 7.86-7.88 (m, 1H), 7.60-7.64 (m, 1H), 7.54-7.58 (m, 2H), 7.47-7.51 (m, 1H), 7.46 (d, J=9.4 Hz, 1H), 7.42 (d, J=7.6 Hz, 1H).

Example 28

N-[3-(imidazo[1,2-b]pyridazin-6-ylethynyl)phenyl]-4-methylbenzamide

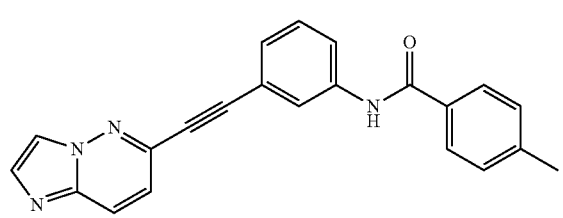 [SMILES: Cc1ccc(C(=O)Nc2cccc(C#Cc3ccc4nccn4n3)c2)cc1]

The compound of Example 28 was made in a manner analogous to Example 17 (see also Schemes 5, 6, 7, and 8).

N-[3-(imidazo[1,2-b]pyridazin-6-ylethynyl)phenyl]-4-methylbenzamide

Example 28

$^1$H NMR (DMSO-d$_6$) δ: 10.33 (s, 1H), 8.36 (s, 1H), 8.20 (d, J=9.4 Hz, 1H), 8.18 (t, J=1.8 Hz, 1H), 7.88-7.91 (m, 3H), 7.85-7.88 (m, 1H), 7.44-7.50 (m, 2H), 7.41 (d, J=7.6 Hz, 1H), 7.36 (d, J=7.9 Hz, 2H), 2.40 (s, 3H).

Example 29

1-(2-fluoro-5-methylphenyl)-3-[3-(imidazo[1,2-b]pyridazin-6-ylethynyl)phenyl]urea

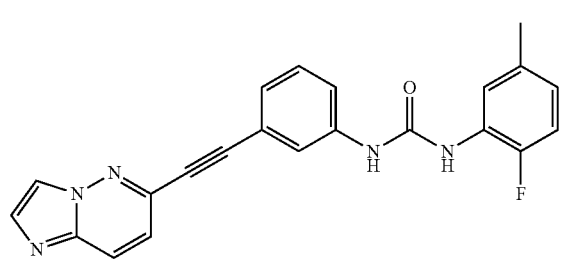 [SMILES: Cc1ccc(F)c(NC(=O)Nc2cccc(C#Cc3ccc4nccn4n3)c2)c1]

The compound of Example 29 was made in a manner analogous to Example 1 (see also Schemes 1, 2, and 9).

1-(2-fluoro-5-methylphenyl)-3-[3-(imidazo[1,2-b]pyridazin-6-ylethynyl)phenyl]urea

Example 29

$^1$H NMR (DMSO-d$_6$) δ: 9.37 (s, 1H), 8.35 (s, 1H), 8.20 (d, J=9.4 Hz, 1H), 8.13 (s, 1H), 7.94-7.97 (m, 1H), 7.89 (s, 1H), 7.84 (dd, J=12.2, 2.8 Hz, 1H), 7.40-7.48 (m, 3H), 7.28-7.32 (m, 1H), 7.16-7.23 (m, 1H), 6.77 (td, J=8.4, 2.6 Hz, 1H), 2.23 (s, 3H).

Example 30

1-(2-fluoro-5-methylphenyl)-3-[2-(imidazo[1,2-b]pyridazin-6-ylethynyl)phenyl]urea

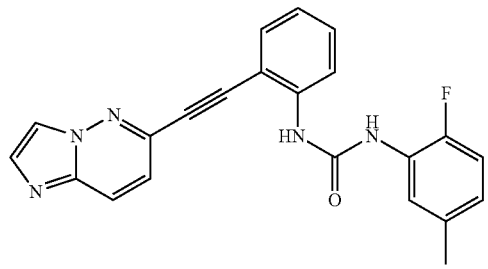 [SMILES: Cc1ccc(F)c(NC(=O)Nc2ccccc2C#Cc2ccc3nccn3n2)c1]

The compound of Example 30 was made in a manner analogous to Example 1 (see also Schemes 1, 2, and 9).

1-(2-fluoro-5-methylphenyl)-3-[2-(imidazo[1,2-b]pyridazin-6-ylethynyl)phenyl]urea

Example 30

$^1$H NMR (DMSO-d$_6$) δ: 9.25 (s, 1H), 8.57 (d, J=2.1 Hz, 1H), 8.35 (s, 1H), 8.20 (d, J=9.7 Hz, 1H), 7.99 (dd, J=7.9, 1.8 Hz, 1H), 7.92-7.96 (m, 1H), 7.89 (s, 1H), 7.40-7.49 (m, 3H), 7.30 (ddd, J=5.7, 2.9, 1.6 Hz, 1H), 7.12 (dd, J=11.4, 8.2 Hz, 1H), 6.79-6.86 (m, 1H), 2.28 (s, 3H).

Example 31

1-{3-[(3-amino-1H-indazol-4-yl)ethynyl]phenyl}-3-(2-fluoro-5-methylphenyl)urea

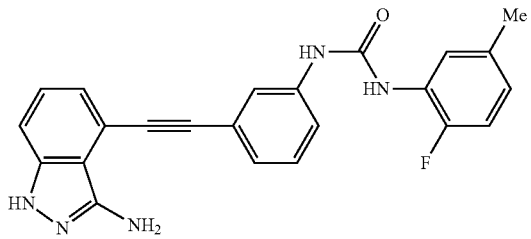

To a mixture of 2-Fluoro-6-iodibenzonitrile (2 g, 8.1 mmol) in 40 ml of n-butanol was added hydrazine monohydrate (4 ml). The reaction was equipped with a reflux condenser and stirred at 110° C. for 5 hours. Next, the reaction was cooled to room temperature, poured into water and extracted with ethyl acetate. The ethyl acetate layer was washed with brine, dried using anhydrous sodium sulfate, and concentrated to give 1.4 g of 4-iodo-1H-indazol-3-amine.

To 8 ml of DMF was added 4-iodo-1H-indazol-3-amine (690 mg, 2.65 mmol) and 3-ethynylaniline (480 mg, 1.5 eq., 4.1 mmol). Following that, Bis(triphenylphosphine) palladium(II) dichloride (180 mg, 0.25 mmol, 10 mol %), Copper Iodide (100 mg, 0.52 mmol, 20 mol %), Triphenylphosphine (18 mg, 0.07 mmol, 3 mol %) and 8 ml of triethylamine was added. Nitrogen was bubbled through the reaction mixture for 15 minutes. The reaction was then set with a reflux condenser, set under nitrogen atmosphere, and heated at 60° C. for 2 hours. After that, the reaction was cooled to room temperature and 40 ml of ethyl acetate was added. The organic layer was extracted with aqueous sodium bicarbonate (3×40 ml), brine (3×40 ml), dried using anhydrous sodium sulfate, loaded onto silica and columned to give 4-((3-aminophenyl)ethynyl)-1H-indazol-3-amine.

4-((3-aminophenyl)ethynyl)-1H-indazol-3-amine (50 mg, 0.2 mmol) was taken in 2 ml of tetrahydrofuran, reaction was set under nitrogen atmosphere. 2-fluoro-1-isocyanato-4-methylbenzene was taken in 1 ml of tetrahydrofuran and added dropwise to the solution of 4-((3-aminophenyl)ethynyl)-1H-indazol-3-amine in tetrahydrofuran. The reaction was stirred at room temperature for 30 min, loaded onto silica and columned to give 1-{3-[(3-amino-1H-indazol-4-yl)ethynyl]phenyl}-3-(2-fluoro-5-methylphenyl)urea.

1-{3-[(3-amino-1H-indazol-4-yl)ethynyl]phenyl}-3-(2-fluoro-5-methylphenyl)urea

Example 31

$^1$H NMR (DMSO-d$_6$) δ: 11.78 (s, 1H), 9.22 (s, 1H), 8.53 (d, J=2.6 Hz, 1H), 7.97 (dd, J=7.9, 2.1 Hz, 1H), 7.78 (t, J=1.6 Hz, 1H), 7.21-7.44 (m, 5H), 7.06-7.15 (m, 2H), 6.76-6.84 (m, 1H), 5.12 (s, 2H), 2.26 (s, 3H).

Example 32

1-{3-[(3-amino-1H-indazol-4-yl)ethynyl]phenyl}-3-phenylurea

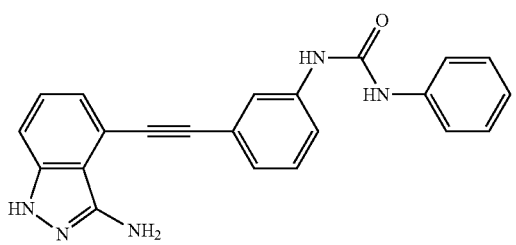 [SMILES: Nc1n[nH]c2cccc(C#Cc3cccc(NC(=O)Nc4ccccc4)c3)c12]

The compound of Example 32 was made in a manner analogous to Example 31 (see also Scheme 10).

1-{3-[(3-amino-1H-indazol-4-yl)ethynyl]phenyl}-3-phenylurea

Example 32

1H NMR (DMSO-d6) δ: 11.78 (s, 1H), 8.84 (s, 1H), 8.73 (s, 1H), 7.76 (t, J=1.8 Hz, 1H), 7.46 (q, J=1.6 Hz, 1H), 7.42-7.46 (m, 2H), 7.19-7.39 (m, 6H), 7.13 (dd, J=6.7, 1.2 Hz, 1H), 6.97 (t, J=7.3 Hz, 1H), 5.12 (s, 2H).

Example 33

1-{4-[(3-amino-1H-indazol-4-yl)ethynyl]phenyl}-3-(2-fluoro-5-methylphenyl)urea

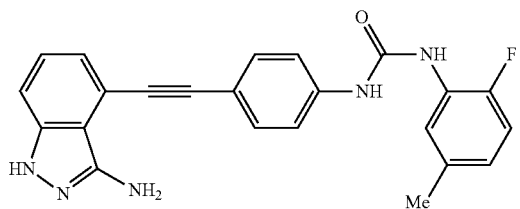 [SMILES: Cc1ccc(F)c(NC(=O)Nc2ccc(C#Cc3cccc4[nH]nc(N)c34)cc2)c1]

The compound of Example 32 was made in a manner analogous to Example 31 (see also Scheme 10).

1-{4-[(3-amino-1H-indazol-4-yl)ethynyl]phenyl}-3-(2-fluoro-5-methylphenyl)urea

Example 33

$^1$H NMR (DMSO-d$_6$) δ: 11.74 (s, 1H), 9.29 (s, 1H), 8.53 (d, J=2.3 Hz, 1H), 7.96 (dd, J=7.6, 2.1 Hz, 1H), 7.52-7.55 (s, 4H), 7.19-7.33 (m, 2H), 7.05-7.13 (m, 2H), 6.76-6.84 (m, 1H), 5.10 (s, 2H), 2.26 (s, 3H).

Biological Data

VEGFR2 Kinase Assay:

Biochemical KDR kinase assays were performed in 96 well microtiter plates that were coated overnight with 75 μg/well of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 μL reaction volumes containing 2.7 μM ATP in kinase buffer (50 mM Hepes buffer pH 7.4, 20 mM MgCl$_2$, 0.1 mM MnCl$_2$ and 0.2 mM Na$_3$VO$_4$). Test compounds were reconstituted in 100% DMSO and added to the reaction to give a final DMSO concentration of 5%. Reactions were initiated by the addition 20 μl per well of kinase buffer containing 200-300 ng purified cytoplasmic domain KDR protein (BPS Bioscience, San Diego, Calif.). Following a 15 minute incubation at 30° C., the reactions were washed 2 mls per well PBS-T. 100 μl of a monoclonal anti-phosphotyrosine antibody-peroxidase conjugate diluted 1:10,000 in PBS-T was added to the wells for 30 minutes. Following a 2 mls per well wash with PBS-Tween-20, 100 μl of O-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 μl of 2.5N H$_2$SO$_4$ to each well and read using a microplate ELISA reader set at 492 nm. IC$_{50}$ values for compound inhibition were calculated directly from graphs of optical density (arbitrary units) versus compound concentration following subtraction of blank values.

VEGFR2 Cellular Assay

Automated FLIPR (Fluorometric Imaging Plate Reader) technology was used to screen for inhibitors of VEGF induced increases in intracellular calcium levels in fluorescent dye loaded endothelial cells. HUVEC (human umbilical vein endothelial cells) (Clonetics) were seeded in 384-well fibronectin coated black-walled plates overnight at 37° C./5% CO2. Cells were loaded with calcium indicator Fluo-4 for 45 minutes at 37° C. Cells were washed 2 times (Elx405, Biotek Instruments) to remove extracellular dye. For screening, cells were pre-incubated with test agents for 30 minutes, at a single concentration (10 µM) or at concentrations ranging from 0.0001 to 10.0 µM followed by $VEGF_{165}$ stimulation (10 ng/mL). Changes in fluorescence at 516 nm were measured simultaneously in all 384 wells using a cooled CCD camera. Data were generated by determining max-min fluorescence levels for unstimulated, stimulated, and drug treated samples. $IC_{50}$ values for test compounds were calculated from % inhibition of VEGF stimulated responses in the absence of inhibitor.

PDGFRβ Kinase Assay

Biochemical PDGFRβ kinase assays were performed in 96 well microtiter plates that were coated overnight with 75 µg of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 µL reaction volumes containing 36 µM ATP in kinase buffer (50 mM Hepes buffer pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 20 µl per well of kinase buffer containing 200-300 ng purified cytoplasmic domain PDGFR-b protein (Millipore). Following a 60 minute incubation at 30° C., the reactions were washed 2 mls per well PBS-T. 100 µl of a monoclonal anti-phosphotyrosine antibody-peroxidase conjugate diluted 1:10,000 in PBS-T was added to the wells for 30 minutes. Following a 2 mls per well wash with PBS-Tween-20, 100 µl of O-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 µl of 2.5N $H_2SO_4$ to each well and read using a microplate ELISA reader set at 492 nm. $IC_{50}$ values for compound inhibition were calculated directly from graphs of optical density (arbitrary units) versus compound concentration following subtraction of blank values.

PDGFRβ Cellular Assay

Automated FLIPR (Fluorometric Imaging Plate Reader) technology was used to screen for inhibitors of PDGF-induced increases in intracellular calcium levels in fluorescent dye loaded endothelial cells. NHDF-Ad (Normal Human Dermal Fibroblasts, Adult; Lonza) were seeded in 384-well fibronectin coated black-walled plates overnight at 37° C./5% CO2. Cells were loaded with calcium indicator Fluo-4 for 45 minutes at 37° C. Cells were washed 2 times (Elx405, Biotek Instruments) to remove extracellular dye. For screening, cells were pre-incubated with test agents for 30 minutes, at a single concentration (10 µM) or at concentrations ranging from 0.0001 to 10.0 µM followed by PDGF-BB stimulation (30 ng/mL). Changes in fluorescence at 516 nm were measured simultaneously in all 384 wells using a cooled CCD camera. Data were generated by determining max-min fluorescence levels for unstimulated, stimulated, and drug treated samples. $IC_{50}$ values for test compounds were calculated from % inhibition of PDGF-BB stimulated responses in the absence of inhibitor.

Results of the assays can be seen in Table 1.

TABLE 1

| Structure | Ex. | Enzyme VEGFR2 IC50 (nM) | Enzyme PDGFRβ IC50 (nM) | Receptor VEGFR2 IC50 (nM) | Receptor PDGFRβ IC50 (nM) |
| --- | --- | --- | --- | --- | --- |
| 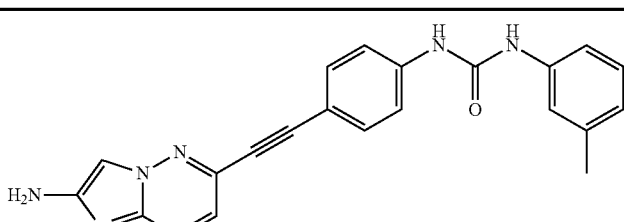 | 1 | 20 | 34 | 51 | 227 |
| 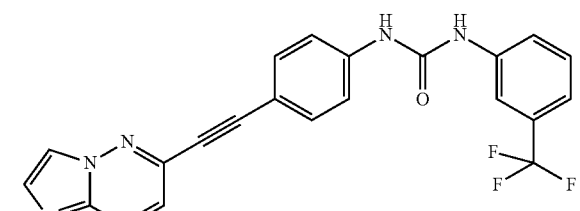 | 2 | 47 | 32 | 962 | 457 |
| 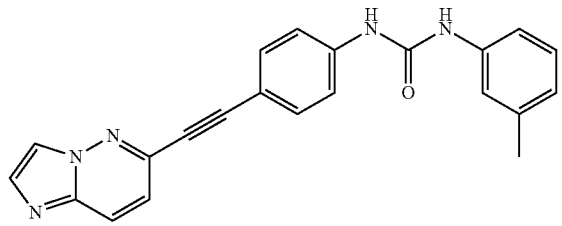 | 3 | 23 | 80 | 132 | 70 |

TABLE 1-continued

| Structure | Ex. | Enzyme VEGFR2 IC50 (nM) | Enzyme PDGFRβ IC50 (nM) | Receptor VEGFR2 IC50 (nM) | Receptor PDGFRβ IC50 (nM) |
| --- | --- | --- | --- | --- | --- |
| 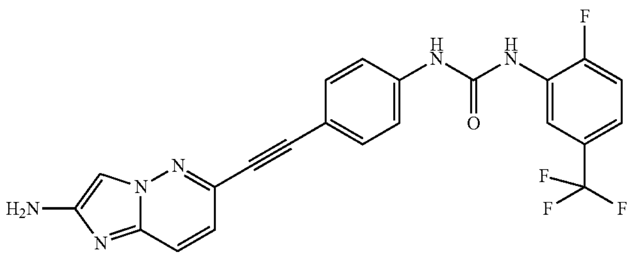 [SMILES: Nc1cn2nc(C#Cc3ccc(NC(=O)Nc4cc(C(F)(F)F)ccc4F)cc3)ccc2n1] | 4 | 73 | 55 | 423 | 516 |
| 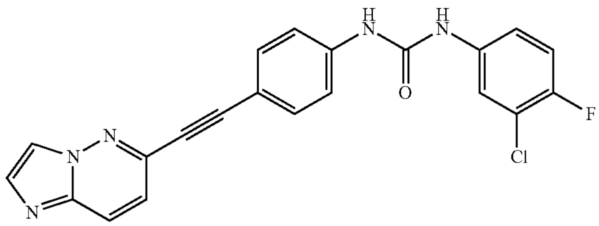 [SMILES: O=C(Nc1ccc(C#Cc2ccc3nccn3n2)cc1)Nc1ccc(F)c(Cl)c1] | 5 | 96 | | | N/A |
| 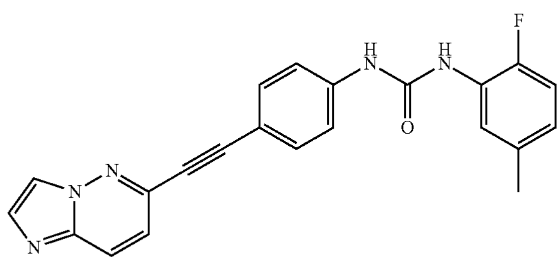 [SMILES: Cc1ccc(F)c(NC(=O)Nc2ccc(C#Cc3ccc4nccn4n3)cc2)c1] | 6 | 101 | | N/A | N/A |
| 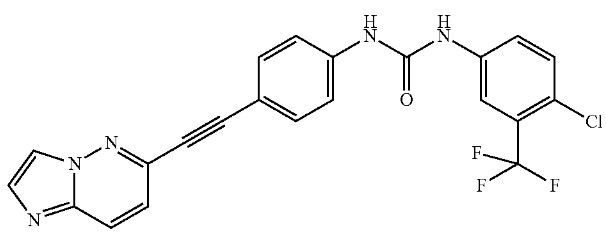 [SMILES: O=C(Nc1ccc(C#Cc2ccc3nccn3n2)cc1)Nc1ccc(Cl)c(C(F)(F)F)c1] | 7 | 127 | 43 | 2046 | N/A |
| 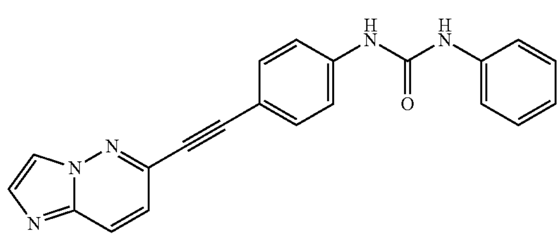 [SMILES: O=C(Nc1ccccc1)Nc1ccc(C#Cc2ccc3nccn3n2)cc1] | 8 | 267 | 185 | 5428 | N/A |
| 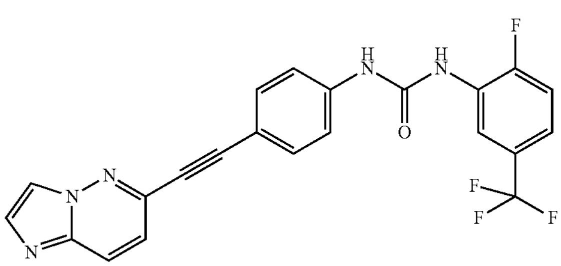 [SMILES: O=C(Nc1ccc(C#Cc2ccc3nccn3n2)cc1)Nc1cc(C(F)(F)F)ccc1F] | 9 | 448 | 93 | 8416 | N/A |

TABLE 1-continued

| Structure | Ex. | Enzyme VEGFR2 IC50 (nM) | Enzyme PDGFRβ IC50 (nM) | Receptor VEGFR2 IC50 (nM) | Receptor PDGFRβ IC50 (nM) |
| --- | --- | --- | --- | --- | --- |
| 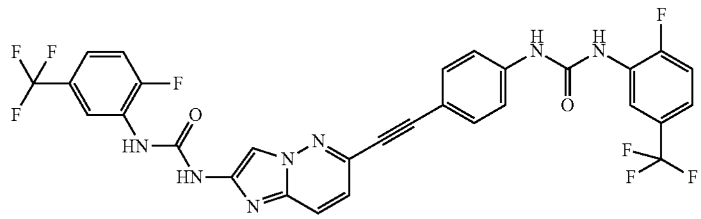 [SMILES: O=C(Nc1ccc(C#Cc2ccc3nc(NC(=O)Nc4cc(C(F)(F)F)ccc4F)cn3n2)cc1)Nc1cc(C(F)(F)F)ccc1F] | 10 | 1433 | >10,000 | >10,000 | >10,000 |
| 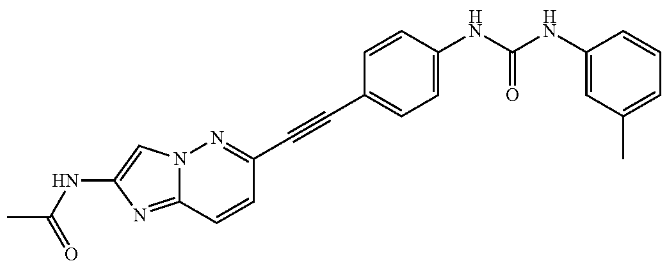 [SMILES: CC(=O)Nc1cn2nc(C#Cc3ccc(NC(=O)Nc4cccc(C)c4)cc3)ccc2n1] | 11 | 3177 | N/A | >10,000 | >10,000 |
| 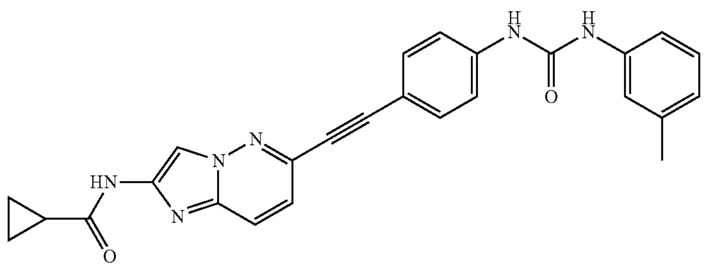 [SMILES: Cc1cccc(NC(=O)Nc2ccc(C#Cc3ccc4nc(NC(=O)C5CC5)cn4n3)cc2)c1] | 12 | 1308 | N/A | >10,000 | >10,000 |
| 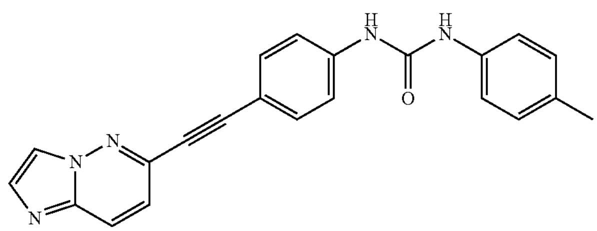 [SMILES: Cc1ccc(NC(=O)Nc2ccc(C#Cc3ccc4nccn4n3)cc2)cc1] | 13 | 2297 | 67 | >10,000 | N/A |
| 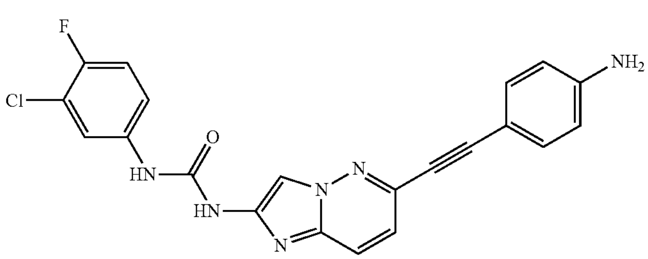 [SMILES: Nc1ccc(C#Cc2ccc3nc(NC(=O)Nc4ccc(F)c(Cl)c4)cn3n2)cc1] | 14 | 1688 | 6574 | >10,000 | 10490 |
| 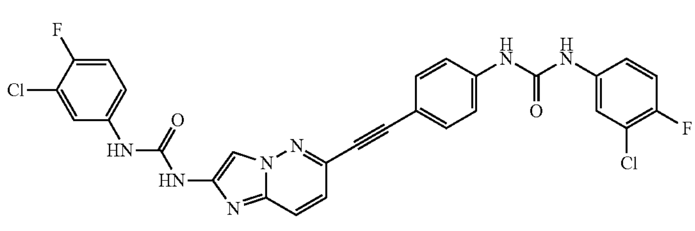 [SMILES: O=C(Nc1ccc(C#Cc2ccc3nc(NC(=O)Nc4ccc(F)c(Cl)c4)cn3n2)cc1)Nc1ccc(F)c(Cl)c1] | 15 | 2934 | 3610 | >10,000 | 3634 |

TABLE 1-continued

| Structure | Ex. | Enzyme VEGFR2 IC50 (nM) | Enzyme PDGFRβ IC50 (nM) | Receptor VEGFR2 IC50 (nM) | Receptor PDGFRβ IC50 (nM) |
|---|---|---|---|---|---|
| 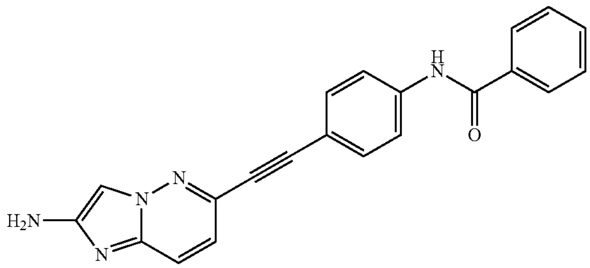 [SMILES: Nc1cn2nc(C#Cc3ccc(NC(=O)c4ccccc4)cc3)ccc2n1] | 19 | 1248 | >10,000 | >10,000 | >10,000 |
| 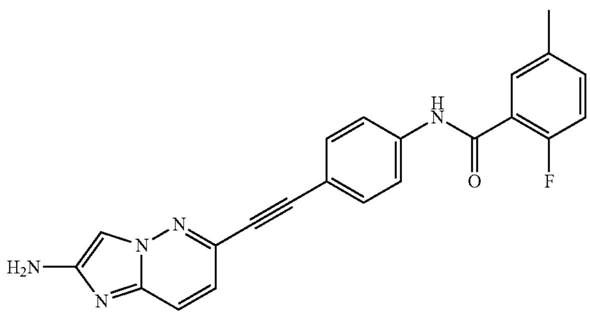 [SMILES: Cc1ccc(F)c(C(=O)Nc2ccc(C#Cc3ccc4nc(N)cn4n3)cc2)c1] | 20 | >10,000 | >10,000 | 4404 | >10,000 |
| 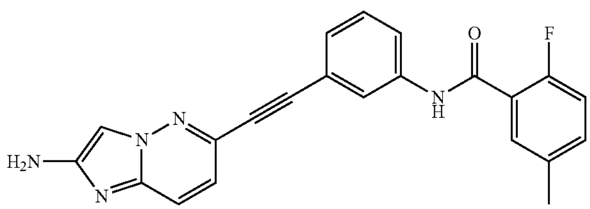 [SMILES: Cc1ccc(F)c(C(=O)Nc2cccc(C#Cc3ccc4nc(N)cn4n3)c2)c1] | 21 | 88 | 767 | 1121 | 371 |
| 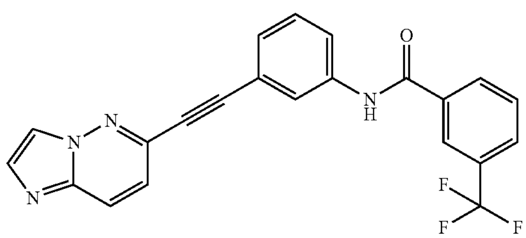 [SMILES: O=C(Nc1cccc(C#Cc2ccc3nccn3n2)c1)c1cccc(C(F)(F)F)c1] | 22 | 279 | 628 | 1280 | 1628 |
| 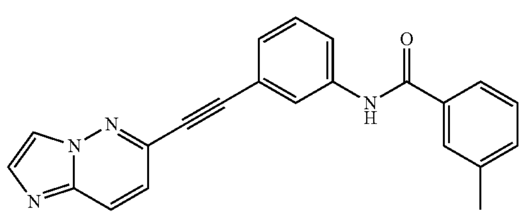 [SMILES: Cc1cccc(C(=O)Nc2cccc(C#Cc3ccc4nccn4n3)c2)c1] | 23 | 295 | 1531 | 862 | N/A |
| 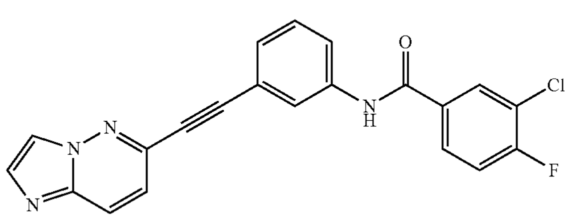 [SMILES: O=C(Nc1cccc(C#Cc2ccc3nccn3n2)c1)c1ccc(F)c(Cl)c1] | 24 | 464 | 938 | 1459 | 2684 |

TABLE 1-continued

| Structure | Ex. | Enzyme VEGFR2 IC50 (nM) | Enzyme PDGFRβ IC50 (nM) | Receptor VEGFR2 IC50 (nM) | Receptor PDGFRβ IC50 (nM) |
|---|---|---|---|---|---|
| 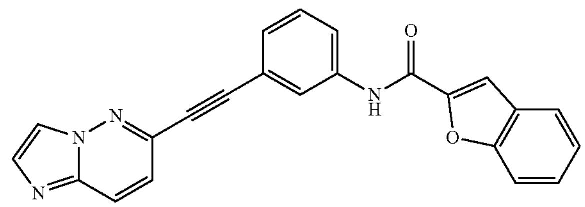 [SMILES: O=C(Nc1cccc(C#Cc2ccc3nccn3n2)c1)c1cc2ccccc2o1] | 25 | 1607 | 2715 | >10,000 | >10,000 |
| 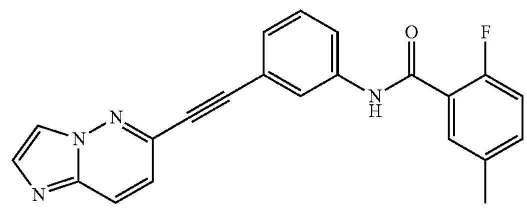 [SMILES: Cc1ccc(F)c(C(=O)Nc2cccc(C#Cc3ccc4nccn4n3)c2)c1] | 26 | 1617 | 6083 | 3038 | >10,000 |
| 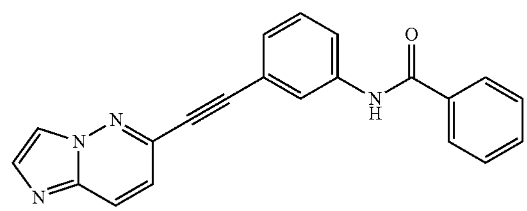 [SMILES: O=C(Nc1cccc(C#Cc2ccc3nccn3n2)c1)c1ccccc1] | 27 | 2363 | 27 | >10,000 | 17766 |
| 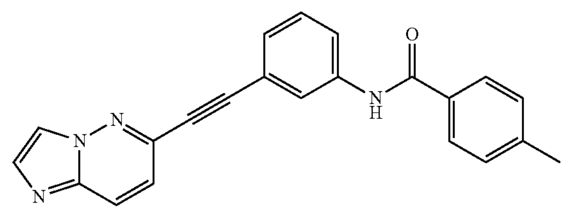 [SMILES: Cc1ccc(C(=O)Nc2cccc(C#Cc3ccc4nccn4n3)c2)cc1] | 28 | 3244 | 4313 | >10,000 | 26893 |
| 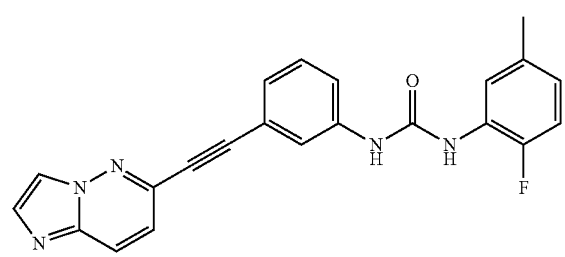 [SMILES: Cc1ccc(F)c(NC(=O)Nc2cccc(C#Cc3ccc4nccn4n3)c2)c1] | 29 | 4695 | >10,000 | N/A | N/A |
| 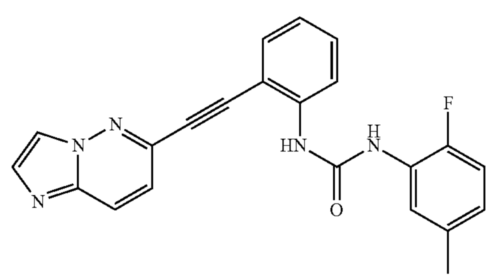 [SMILES: Cc1ccc(F)c(NC(=O)Nc2ccccc2C#Cc2ccc3nccn3n2)c1] | 30 | 1805 | >10,000 | | |

TABLE 1-continued

| Structure | Ex. | Enzyme VEGFR2 IC50 (nM) | Enzyme PDGFRβ IC50 (nM) | Receptor VEGFR2 IC50 (nM) | Receptor PDGFRβ IC50 (nM) |
|---|---|---|---|---|---|
| 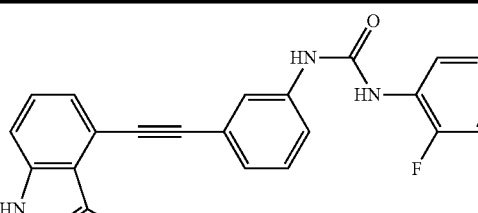 | 31 | 21 | N/A | 16 | N/A |
| 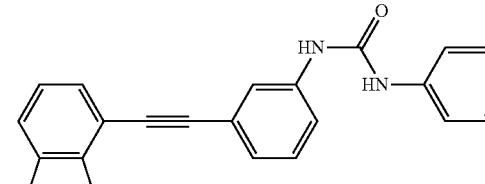 | 32 | 41 | N/A | 20 | N/A |
| 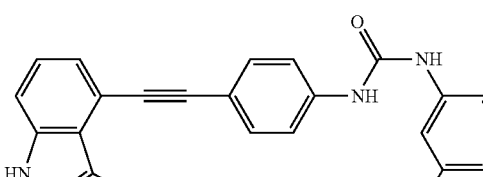 | 33 | 90 | N/A | 162 | N/A |

Ex.: Example (see synthetic examples);
N/A: not acquired

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention can contain one or more asymmetric centers, such that the compounds can exist in enantiomeric as well as in diastereomeric forms. Unless it is specifically noted otherwise, the scope of the present invention includes all enantiomers, diastereomers and racemic mixtures. Some of the compounds of the invention can form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention can contain one or more isotopic atoms enriched or different than the natural ratio such as deuterium $^2H$ (or D) in place of hydrogen $^1H$ (or H) or use of $^{13}C$ enriched material in place of $^{12}C$ and the like. Similar substitutions can be employed for N, O and S. The use of isotopes can assist in analytical as well as therapeutic aspects of the invention. For example, use of deuterium can increase the in vivo half-life by altering the metabolism (rate) of the compounds of the invention. These compounds can be prepared in accord with the preparations described by use of isotopically enriched reagents.

As will be evident to those skilled in the art, individual isomeric forms can be obtained by separation of mixtures thereof in conventional manner. For example, in the case of diasteroisomeric isomers, chromatographic separation can be employed.

Compound names were generated with ACDLabs version 12.5. Some of the intermediate and reagent names used in the examples were generated with software such as Chem Bio Draw Ultra version 12.0 or Auto Nom 2000 from MDL ISIS Draw 2.5 SP1.

What is claimed is:

1. A compound represented by Formula III or V:

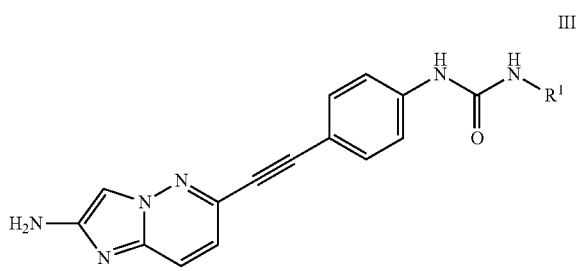

III

-continued

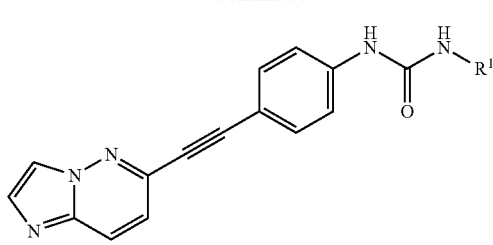

V or a pharmaceutically acceptable salt thereof, wherein:
$R^1$ is represented by Formula IV:

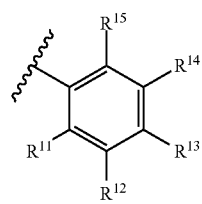

IV wherein $R^{11}$ to $R^{15}$ are independently selected from the group consisting of hydrogen, methyl, trifluoromethyl, $OR^{16}$, $N(R^{17})R^{18}$, and halogen, wherein $R^{16}$ to $R^{18}$ are independently $C_1$ to $C_8$ alkyl.

2. The compound of claim 1, wherein the A compound selected from the group consisting of:
   1-{4-[(2-aminoimidazo[1,2-b]pyridazin-6-yl)ethynyl]phenyl}-3-(3-methylphenyl)urea;
   1-[4-(imidazo[1,2-b]pyridazin-6-ylethynyl)phenyl]-3-[3-(trifluoromethyl)phenyl]urea;
   1-[4-(imidazo[1,2-b]pyridazin-6-ylethynyl)phenyl]-3-(3-methylphenyl)urea
   1-{4-[(2-aminoimidazo[1,2-b]pyridazin-6-yl)ethynyl]phenyl}-3-[2-fluoro-5-(trifluoromethyl)phenyl]urea;
   1-(3-chloro-4-fluorophenyl)-3-[4-(imidazo[1,2-b]pyridazin-6-ylethynyl)phenyl]urea;
   1-(2-fluoro-5-methylphenyl)-3-[4-(imidazo[1,2-b]pyridazin-6-ylethynyl)phenyl]urea;
   1-[4-chloro-3-(trifluoromethyl)phenyl]-3-[4-(imidazo[1,2-b]pyridazin-6-ylethynyl)phenyl]urea;
   1-[4-(imidazo[1,2-b]pyridazin-6-ylethynyl)phenyl]-3-phenylurea;
   1-[2-fluoro-5-(trifluoromethyl)phenyl]-3-[4-(imidazo[1,2-b]pyridazin-6-ylethynyl)phenyl]urea;
   1-[2-fluoro-5-(trifluoromethyl)phenyl]-3-[4-({2-[({[2-fluoro-5-(trifluoromethyl)phenyl]amino}carbonyl)amino]imidazo[1,2-b]pyridazin-6-yl}ethynyl)phenyl]urea;
   N-(6-{[4-({[(3-methylphenyl)amino]carbonyl}amino)phenyl]ethynyl}imidazo[1,2-b]pyridazin-2-yl)acetamide;
   N-(6-{[4-({[(3-methylphenyl)amino]carbonyl}amino)phenyl]ethynyl}imidazo[1,2-b]pyridazin-2-yl)cyclopropanecarboxamide;
   1-[4-(imidazo[1,2-b]pyridazin-6-ylethynyl)phenyl]-3-(4-methylphenyl)urea;
   1-{6-[(4-aminophenyl)ethynyl]imidazo[1,2-b]pyridazin-2-yl}-3-(3-chloro-4-fluorophenyl)urea;
   1-(3-chloro-4-fluorophenyl)-3-(4-{[2-({[(3-chloro-4-fluorophenyl)amino]carbonyl}amino)imidazo[1,2-b]pyridazin-6-yl]ethynyl}phenyl)urea;

N-{4-[(2-aminoimidazo[1,2-b]pyridazin-6-yl)ethynyl]phenyl}benzamide;
   N-{4-[(2-aminoimidazo[1,2-b]pyridazin-6-yl)ethynyl]phenyl}-2-fluoro-5-methylbenzamide;
   N-{3-[(2-aminoimidazo[1,2-b]pyridazin-6-yl)ethynyl]phenyl}-2-fluoro-5-methylbenzamide;
   N-[3-(imidazo[1,2-b]pyridazin-6-ylethynyl)phenyl]-3-(trifluoromethyl)benzamide;
   N-[3-(imidazo[1,2-b]pyridazin-6-ylethynyl)phenyl]-3-methylbenzamide;
   3-chloro-4-fluoro-N-[3-(imidazo[1,2-b]pyridazin-6-ylethynyl)phenyl]benzamide;
   N-[3-(imidazo[1,2-b]pyridazin-6-ylethynyl)phenyl]-1-benzofuran-2-carboxamide;
   2-fluoro-N-[3-(imidazo[1,2-b]pyridazin-6-ylethynyl)phenyl]-5-methylbenzamide;
   N-[3-(imidazo[1,2-b]pyridazin-6-ylethynyl)phenyl]benzamide;
   N-[3-(imidazo[1,2-b]pyridazin-6-ylethynyl)phenyl]-4-methylbenzamide;
   1-(2-fluoro-5-methylphenyl)-3-[3-(imidazo[1,2-b]pyridazin-6-ylethynyl)phenyl]urea; and
   1-(2-fluoro-5-methylphenyl)-3-[2-(imidazo[1,2-b]pyridazin-6-ylethynyl)phenyl]urea;
   or a pharmaceutically acceptable salt thereof.

3. A pharmaceutical composition comprising as active ingredient a therapeutically effective amount of a compound according to claim 1, or a pharmaceutically acceptable salt thereof, and a pharmaceutically acceptable adjuvant, diluent or carrier.

4. A compound represented by Formula VII:

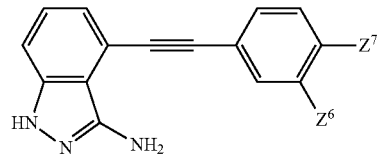

VII or a pharmaceutically acceptable salt thereof, wherein:
one of $Z^6$ and $Z^7$ is independently hydrogen and the other is independently:

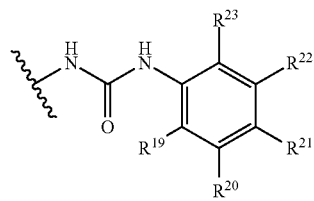

wherein $R^{19}$ to $R^{23}$ are independently selected from the group consisting of hydrogen, methyl, trifluoromethyl, $OR^{24}$, $N(R^{25})R^{26}$, and halogen; $R^{24}$ to $R^{26}$ are independently $C_1$ to $C_8$ alkyl.

5. The compound of claim 4, wherein the compound is selected from the group consisting of:
   1-{3-[(3-amino-1H-indazol-4-yl)ethynyl]phenyl}-3-(2-fluoro-5-methylphenyl)urea;
   1-{3-[(3-amino-1H-indazol-4-yl)ethynyl]phenyl}-3-phenylurea; and 1-{4-[(3-amino-1H-indazol-4-yl)ethynyl]phenyl}-3-(2-fluoro-5-methylphenyl)urea;

or a pharmaceutically acceptable salt thereof.

6. A pharmaceutical composition comprising as active ingredient a therapeutically effective amount of a compound according to claim 4, or a pharmaceutically acceptable salt thereof, and a pharmaceutically acceptable adjuvant, diluent or carrier.

* * * * *

UNITED STATES PATENT AND TRADEMARK OFFICE
CERTIFICATE OF CORRECTION

| | |
|---|---|
| PATENT NO. | : 9,233,968 B1 |
| APPLICATION NO. | : 14/524256 |
| DATED | : January 12, 2016 |
| INVENTOR(S) | : Sougato Boral et al. |

It is certified that error appears in the above-identified patent and that said Letters Patent is hereby corrected as shown below:

On the Title page, in item (56), in column 2, under "Other Publications", line 15, delete "R." and insert -- R., --, therefor.

Specification

In column 2, line 16, after "2625" insert -- . --.

In column 2, line 20, delete "Opthalmologica" and insert -- Ophthalmologica --, therefor.

In column 3, line 49, delete "$C_8$," and insert -- $C_8$ --, therefor.

In column 8, line 9, delete "$C_8$," and insert -- $C_8$ --, therefor.

In column 8, line 9, delete "alkyl," and insert -- alkyl; --, therefor.

In column 9, line 1, delete "pyrdinyl" and insert -- pyridinyl --, therefor.

In column 14, line 40, delete "$OR^7$,)" and insert -- $OR^7$, --, therefor.

In column 26, line 41, delete "Foe" and insert -- For --, therefor.

In column 54, line 55, delete "iodibenzonitrile" and insert -- iodobenzonitrile --, therefor.

In column 55, line 65, delete "1H" and insert -- $^1H$ --, therefor.

In column 68, line 42, delete "diasteroisomeric" and insert -- diastereoisomeric --, therefor.

Claims

In column 69, line 30, in Claim 2, before "A" delete "The compound of claim 1, wherein the".

In column 69, line 38, in Claim 2, after "urea" insert -- ; --.

Signed and Sealed this
Nineteenth Day of April, 2016

Michelle K. Lee
*Director of the United States Patent and Trademark Office*